(12) United States Patent
Dewey et al.

(10) Patent No.: US 12,239,544 B2
(45) Date of Patent: Mar. 4, 2025

(54) RHOMBOID SHAPED IMPLANTS

(71) Applicant: Warsaw Orthopedic, Inc., Warsaw, IN (US)

(72) Inventors: Jonathan M. Dewey, Memphis, TN (US); Joshua A. Ruth, Edina, MN (US); Julien J. Prevost, Memphis, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 888 days.

(21) Appl. No.: 17/332,284

(22) Filed: May 27, 2021

(65) Prior Publication Data

US 2022/0133488 A1 May 5, 2022

Related U.S. Application Data

(63) Continuation-in-part of application No. 17/331,058, filed on May 26, 2021, now Pat. No. 11,517,443, and
(Continued)

(30) Foreign Application Priority Data

Nov. 5, 2020 (WO) .................. PCT/IB2020/000942
Nov. 5, 2020 (WO) .................. PCT/IB2020/000953

(51) Int. Cl.
*A61F 2/44* (2006.01)
*A61F 2/30* (2006.01)

(52) U.S. Cl.
CPC .............. *A61F 2/442* (2013.01); *A61F 2/447* (2013.01); *A61F 2002/30151* (2013.01); *A61F 2002/30433* (2013.01)

(58) Field of Classification Search
CPC ................................. A61F 2/4455; A61F 2/447
See application file for complete search history.

(56) References Cited

U.S. PATENT DOCUMENTS 1,677,337 A 7/1928 Grove
3,847,154 A 11/1974 Nordin
(Continued)

FOREIGN PATENT DOCUMENTS

CN 107 137 166 A 9/2017
DE 44 16 605 C1 6/1995
(Continued)

OTHER PUBLICATIONS

International Search Report and Written Opinion in Application No. PCT/IB2023/058417 dated Dec. 7, 2023.
(Continued)

*Primary Examiner* — Ellen C Hammond
(74) *Attorney, Agent, or Firm* — FOX ROTHSCHILD LLP

(57) ABSTRACT

A rhomboid shaped spinal implant may include a proximal surface that extends from a first lower end to a first upper end thereof a first distance, and a distal surface that extends from a second lower end to a second upper end thereof a second distance. The implant may include a superior surface that extends from the first upper end of the proximal surface to the second upper end of the distal surface a third distance, and an inferior surface that extends from the first lower end of the proximal surface to the second lower end of the distal surface a fourth distance. In various embodiments, the first distance is greater than the second distance, and the third distance is less than the fourth distance. In some embodiments, at least one bone screw aperture defines a trajectory extending in a direction substantially perpendicular to the superior and/or inferior surface.

16 Claims, 9 Drawing Sheets

Related U.S. Application Data a continuation-in-part of application No. 17/307,578, filed on May 4, 2021, now Pat. No. 11,395,743, and a continuation-in-part of application No. 17/246,968, filed on May 3, 2021, now Pat. No. 11,291,554, said application No. 17/331,058 is a continuation-in-part of application No. 17/123,889, filed on Dec. 16, 2020.

(56) References Cited

U.S. PATENT DOCUMENTS

| | | |
|---|---|---|
| 4,401,112 A | 8/1983 | Rezaian |
| 4,553,273 A | 11/1985 | Wu |
| 4,636,217 A | 1/1987 | Ogilvie et al. |
| 4,716,894 A | 1/1988 | Lazzeri et al. |
| 4,759,769 A | 7/1988 | Hedman et al. |
| 5,059,193 A | 10/1991 | Kuslich |
| 5,171,278 A | 12/1992 | Pisharodi |
| 5,228,811 A | 7/1993 | Potter |
| 5,284,483 A | 2/1994 | Johnson et al. |
| 5,336,223 A | 8/1994 | Rogers |
| 5,390,683 A | 2/1995 | Pisharodi |
| 5,522,899 A | 6/1996 | Michelson |
| 5,554,191 A | 9/1996 | Lahille et al. |
| 5,575,790 A | 11/1996 | Chen et al. |
| 5,609,635 A | 3/1997 | Michelson |
| 5,653,762 A | 8/1997 | Pisharodi |
| 5,653,763 A | 8/1997 | Errico et al. |
| 5,658,336 A | 8/1997 | Pisharodi |
| 5,665,122 A | 9/1997 | Kambin |
| 5,693,100 A | 12/1997 | Pisharodi |
| 5,697,977 A | 12/1997 | Pisharodi |
| 5,702,391 A | 12/1997 | Lin |
| 5,702,453 A | 12/1997 | Rabbe et al. |
| 5,702,455 A | 12/1997 | Saggar |
| 5,797,918 A | 8/1998 | McGuire et al. |
| 5,800,550 A | 9/1998 | Sertich |
| 5,865,848 A | 2/1999 | Baker |
| 5,893,890 A | 4/1999 | Pisharodi |
| 5,931,777 A | 8/1999 | Sava |
| 5,941,885 A | 8/1999 | Jackson |
| 5,971,987 A | 10/1999 | Huxel et al. |
| 5,980,522 A | 11/1999 | Koros et al. |
| 6,045,579 A | 4/2000 | Hochshuler et al. |
| 6,074,343 A | 6/2000 | Nathanson et al. |
| 6,080,193 A | 6/2000 | Hochshuler et al. |
| 6,099,531 A | 8/2000 | Bonutti |
| 6,102,949 A | 8/2000 | Biedermann et al. |
| 6,102,950 A | 8/2000 | Vaccaro |
| 6,106,557 A | 8/2000 | Robioneck et al. |
| 6,113,638 A | 9/2000 | Williams et al. |
| 6,117,174 A | 9/2000 | Nolan |
| 6,132,465 A | 10/2000 | Ray et al. |
| 6,159,211 A | 12/2000 | Boriani et al. |
| 6,159,244 A | 12/2000 | Suddaby |
| 6,176,882 B1 | 1/2001 | Biedermann et al. |
| 6,179,873 B1 | 1/2001 | Zientek |
| 6,190,414 B1 | 2/2001 | Young et al. |
| 6,193,757 B1 | 2/2001 | Foley et al. |
| 6,217,579 B1 | 4/2001 | Koros |
| 6,245,108 B1 | 6/2001 | Biscup |
| 6,309,421 B1 | 10/2001 | Pisharodi |
| 6,342,074 B1 | 1/2002 | Simpson |
| 6,371,989 B1 | 4/2002 | Chauvin et al. |
| 6,395,031 B1 | 5/2002 | Foley et al. |
| 6,423,063 B1 | 7/2002 | Bonutti |
| 6,432,106 B1 | 8/2002 | Fraser |
| 6,436,140 B1 | 8/2002 | Liu et al. |
| 6,443,989 B1 | 9/2002 | Jackson |
| 6,443,990 B1 | 9/2002 | Aebi et al. |
| 6,454,806 B1 | 9/2002 | Cohen et al. |
| 6,454,807 B1 | 9/2002 | Jackson |
| 6,461,359 B1 | 10/2002 | Tribus et al. |
| 6,475,218 B2 | 11/2002 | Gournay et al. |
| 6,491,724 B1 | 12/2002 | Ferree |
| 6,520,991 B2 | 2/2003 | Huene |
| 6,520,993 B2 | 2/2003 | James et al. |
| 6,524,238 B2 | 2/2003 | Velikaris et al. |
| 6,527,803 B1 | 3/2003 | Crozet et al. |
| 6,562,074 B2 | 5/2003 | Gerbec et al. |
| 6,576,016 B1 | 6/2003 | Hochshuler et al. |
| 6,623,525 B2 | 9/2003 | Ralph et al. |
| 6,629,998 B1 | 10/2003 | Lin |
| 6,635,086 B2 | 10/2003 | Lin |
| 6,648,917 B2 | 11/2003 | Gerbec et al. |
| 6,676,703 B2 | 1/2004 | Biscup |
| 6,685,742 B1 | 2/2004 | Jackson |
| 6,723,126 B1 | 4/2004 | Berry |
| 6,770,096 B2 | 8/2004 | Bolger et al. |
| 6,773,460 B2 | 8/2004 | Jackson |
| 6,821,298 B1 | 11/2004 | Jackson |
| 6,835,206 B2 | 12/2004 | Jackson |
| 6,849,093 B2 | 2/2005 | Michelson |
| 6,852,129 B2 | 2/2005 | Gerbec et al. |
| 6,863,673 B2 | 3/2005 | Gerbec et al. |
| 6,923,814 B1 | 8/2005 | Hildebrand et al. |
| 6,926,737 B2 | 8/2005 | Jackson |
| 6,953,477 B2 | 10/2005 | Berry |
| 6,964,687 B1 | 11/2005 | Bernard et al. |
| 6,974,480 B2 | 12/2005 | Messerli et al. |
| 6,984,234 B2 | 1/2006 | Bray |
| 7,112,222 B2 | 9/2006 | Fraser et al. |
| 7,135,043 B2 | 11/2006 | Nakahara et al. |
| 7,137,997 B2 | 11/2006 | Paul |
| 7,172,627 B2 | 2/2007 | Fiere et al. |
| 7,188,626 B2 | 3/2007 | Foley et al. |
| 7,204,853 B2 | 4/2007 | Gordon et al. |
| 7,232,464 B2 | 6/2007 | Mathieu et al. |
| 7,238,203 B2 | 7/2007 | Bagga et al. |
| 7,255,700 B2 | 8/2007 | Kaiser et al. |
| 7,316,532 B2 | 1/2008 | Matthys-Mark |
| 7,316,714 B2 | 1/2008 | Gordon et al. |
| 7,407,483 B2 | 8/2008 | Perez-Cruet et al. |
| 7,481,766 B2 | 1/2009 | Lee et al. |
| 7,491,168 B2 | 2/2009 | Raymond et al. |
| 7,537,565 B2 | 5/2009 | Bass |
| 7,618,456 B2 | 11/2009 | Mathieu et al. |
| 7,625,394 B2 | 12/2009 | Molz, IV et al. |
| 7,635,366 B2 | 12/2009 | Abdou |
| 7,637,909 B2 | 12/2009 | Lechot et al. |
| 7,655,046 B2 | 2/2010 | Dryer et al. |
| 7,678,148 B2 | 3/2010 | Peterman |
| 7,703,727 B2 | 4/2010 | Selness |
| 7,708,778 B2 | 5/2010 | Gordon et al. |
| 7,708,779 B2 | 5/2010 | Edie et al. |
| 7,727,280 B2 | 6/2010 | McLuen |
| 7,753,958 B2 | 7/2010 | Gordon et al. |
| 7,780,594 B2 | 8/2010 | Hutton |
| 7,806,932 B2 | 10/2010 | Webb et al. |
| 7,815,682 B1 | 10/2010 | Peterson et al. |
| 7,819,801 B2 | 10/2010 | Miles et al. |
| 7,824,428 B2 | 11/2010 | Mikkonen et al. |
| 7,828,849 B2 | 11/2010 | Lim |
| 7,846,167 B2 | 12/2010 | Garcia et al. |
| 7,846,207 B2 | 12/2010 | Lechmann et al. |
| 7,850,731 B2 | 12/2010 | Brittan et al. |
| 7,850,733 B2 | 12/2010 | Baynham et al. |
| 7,862,616 B2 | 1/2011 | Lechmann et al. |
| 7,875,076 B2 | 1/2011 | Mathieu et al. |
| 7,883,542 B2 | 2/2011 | Zipnick |
| 7,892,173 B2 | 2/2011 | Miles et al. |
| 7,909,869 B2 | 3/2011 | Gordon et al. |
| 7,914,559 B2 | 3/2011 | Carls et al. |
| 7,967,821 B2 | 6/2011 | Sicvol et al. |
| 7,981,031 B2 | 7/2011 | Frasier et al. |
| 8,016,836 B2 | 9/2011 | Corrao et al. |
| 8,062,375 B2 | 11/2011 | Glerum et al. |
| 8,105,382 B2 | 1/2012 | Olmos et al. |
| 8,118,870 B2 | 2/2012 | Gordon et al. |
| 8,118,871 B2 | 2/2012 | Gordon et al. |
| 8,123,810 B2 | 2/2012 | Gordon et al. |
| 8,147,550 B2 | 4/2012 | Gordon et al. |
| 8,172,903 B2 | 5/2012 | Gordon et al. |
| 8,182,539 B2 | 5/2012 | Tyber et al. |
| 8,257,442 B2 | 9/2012 | Edie et al. |

(56) References Cited

U.S. PATENT DOCUMENTS

| | | |
|---|---|---|
| 8,262,570 B2 | 9/2012 | White et al. |
| 8,262,662 B2 | 9/2012 | Beardsley et al. |
| 8,262,710 B2 | 9/2012 | Freedman et al. |
| 8,287,597 B1 | 10/2012 | Pimenta et al. |
| 8,303,498 B2 | 11/2012 | Miles et al. |
| 8,303,658 B2 | 11/2012 | Peterman |
| 8,303,663 B2 | 11/2012 | Jimenez et al. |
| 8,317,866 B2 | 11/2012 | Palmatier et al. |
| 8,323,185 B2 | 12/2012 | Perez-Cruet et al. |
| 8,328,872 B2 | 12/2012 | Duffield et al. |
| 8,343,048 B2 | 1/2013 | Warren, Jr. |
| 8,353,826 B2 | 1/2013 | Weiman |
| 8,355,780 B2 | 1/2013 | Miles et al. |
| 8,382,842 B2 | 2/2013 | Greenhalgh et al. |
| 8,388,527 B2 | 3/2013 | Miles et al. |
| 8,398,713 B2 | 3/2013 | Weiman |
| 8,403,990 B2 | 3/2013 | Dryer et al. |
| 8,419,797 B2 | 4/2013 | Biedermann et al. |
| 8,425,528 B2 | 4/2013 | Berry et al. |
| 8,435,298 B2 | 5/2013 | Weiman |
| 8,480,576 B2 | 7/2013 | Sandhu |
| 8,496,706 B2 | 7/2013 | Ragab et al. |
| 8,500,634 B2 | 8/2013 | Miles et al. |
| 8,506,635 B2 | 8/2013 | Palmatier et al. |
| 8,517,935 B2 | 8/2013 | Marchek et al. |
| 8,518,120 B2 | 8/2013 | Glerum et al. |
| 8,535,380 B2 | 9/2013 | Greenhalgh et al. |
| 8,550,994 B2 | 10/2013 | Miles et al. |
| 8,556,808 B2 | 10/2013 | Miles et al. |
| 8,556,979 B2 | 10/2013 | Glerum et al. |
| 8,579,809 B2 | 11/2013 | Parker |
| 8,579,898 B2 | 11/2013 | Prandi et al. |
| 8,579,979 B2 | 11/2013 | Edie et al. |
| 8,579,981 B2 | 11/2013 | Lim et al. |
| 8,602,984 B2 | 12/2013 | Raymond et al. |
| 8,608,785 B2 | 12/2013 | Reed et al. |
| 8,628,576 B2 | 1/2014 | Triplett et al. |
| 8,628,578 B2 | 1/2014 | Miller et al. |
| 8,632,595 B2 | 1/2014 | Weiman |
| 8,641,768 B2 | 2/2014 | Duffield et al. |
| 8,647,386 B2 | 2/2014 | Gordon et al. |
| 8,663,329 B2 | 3/2014 | Ernst |
| 8,668,419 B2 | 3/2014 | Hardt et al. |
| 8,668,715 B2 | 3/2014 | Sandhu |
| 8,679,183 B2 | 3/2014 | Glerum et al. |
| 8,685,095 B2 | 4/2014 | Miller et al. |
| 8,685,098 B2 | 4/2014 | Glerum et al. |
| 8,696,559 B2 | 4/2014 | Miles et al. |
| 8,709,083 B2 | 4/2014 | Duffield et al. |
| 8,709,085 B2 | 4/2014 | Lechmann et al. |
| 8,709,086 B2 | 4/2014 | Glerum |
| 8,715,285 B2 | 5/2014 | Lewis et al. |
| 8,715,353 B2 | 5/2014 | Bagga et al. |
| 8,740,983 B1 | 6/2014 | Arnold et al. |
| 8,753,271 B1 | 6/2014 | Miles et al. |
| 8,753,396 B1 | 6/2014 | Hockett et al. |
| 8,764,649 B2 | 7/2014 | Miles et al. |
| 8,771,360 B2 | 7/2014 | Jimenez et al. |
| 8,778,025 B2 | 7/2014 | Ragab et al. |
| 8,778,027 B2 | 7/2014 | Medina |
| 8,795,366 B2 | 8/2014 | Varela |
| 8,808,305 B2 | 8/2014 | Kleiner |
| 8,827,902 B2 | 9/2014 | Dietze, Jr. et al. |
| 8,828,085 B1 | 9/2014 | Jensen |
| 8,840,668 B1 | 9/2014 | Donahoe et al. |
| 8,845,731 B2 | 9/2014 | Weiman |
| 8,845,732 B2 | 9/2014 | Weiman |
| 8,845,734 B2 | 9/2014 | Weiman |
| 8,852,252 B2 | 10/2014 | Venturini et al. |
| 8,852,282 B2 | 10/2014 | Farley et al. |
| 8,864,833 B2 | 10/2014 | Glerum et al. |
| 8,882,813 B2 | 11/2014 | Jones et al. |
| 8,888,853 B2 | 11/2014 | Glerum et al. |
| 8,894,708 B2 | 11/2014 | Thalgott et al. |
| 8,894,711 B2 | 11/2014 | Varela |
| 8,894,712 B2 | 11/2014 | Varela |
| 8,906,095 B2 | 12/2014 | Christensen et al. |
| 8,920,500 B1 | 12/2014 | Pimenta et al. |
| 8,926,704 B2 | 1/2015 | Glerum et al. |
| 8,936,641 B2 | 1/2015 | Cain |
| 8,940,049 B1 | 1/2015 | Jimenez et al. |
| 8,968,363 B2 | 3/2015 | Weiman et al. |
| 8,986,344 B2 | 3/2015 | Sandhu |
| 8,992,425 B2 | 3/2015 | Karpowicz et al. |
| 8,992,544 B2 | 3/2015 | Sasing |
| 9,005,292 B2 | 4/2015 | Melamed |
| 9,005,293 B2 | 4/2015 | Moskowitz et al. |
| 9,005,295 B2 | 4/2015 | Kueenzi et al. |
| 9,017,412 B2 | 4/2015 | Wolters et al. |
| 9,034,045 B2 | 5/2015 | Davenport et al. |
| 9,050,146 B2 | 6/2015 | Woolley et al. |
| 9,050,194 B2 | 6/2015 | Thibodeau |
| 9,060,877 B2 | 6/2015 | Kleiner |
| 9,072,548 B2 | 7/2015 | Matityahu |
| 9,072,563 B2 | 7/2015 | Garcia et al. |
| 9,084,591 B2 | 7/2015 | Reglos et al. |
| 9,113,854 B2 | 8/2015 | Ellman |
| 9,119,730 B2 | 9/2015 | Glerum et al. |
| 9,125,757 B2 | 9/2015 | Weiman |
| 9,132,021 B2 | 9/2015 | Mermuys et al. |
| 9,138,217 B2 | 9/2015 | Smith et al. |
| 9,138,330 B2 | 9/2015 | Hansell et al. |
| 9,138,331 B2 | 9/2015 | Aferzon |
| 9,149,367 B2 | 10/2015 | Davenport et al. |
| 9,155,628 B2 | 10/2015 | Glerum et al. |
| 9,155,631 B2 | 10/2015 | Seifert et al. |
| 9,161,841 B2 | 10/2015 | Kana et al. |
| 9,179,903 B2 | 11/2015 | Cianfrani et al. |
| 9,179,952 B2 | 11/2015 | Biedermann et al. |
| 9,186,193 B2 | 11/2015 | Kleiner et al. |
| 9,186,258 B2 | 11/2015 | Davenport et al. |
| 9,192,482 B1 | 11/2015 | Pimenta et al. |
| 9,192,483 B1 | 11/2015 | Radcliffe et al. |
| 9,198,772 B2 | 12/2015 | Weiman |
| 9,204,972 B2 | 12/2015 | Weiman et al. |
| 9,204,974 B2 | 12/2015 | Glerum et al. |
| 9,211,194 B2 | 12/2015 | Bagga et al. |
| 9,211,196 B2 | 12/2015 | Glerum et al. |
| 9,216,095 B2 | 12/2015 | Glerum et al. |
| 9,226,836 B2 | 1/2016 | Glerum |
| 9,233,007 B2 | 1/2016 | Sungarian et al. |
| 9,233,009 B2 | 1/2016 | Gray et al. |
| 9,233,010 B2 | 1/2016 | Thalgott et al. |
| 9,259,327 B2 | 2/2016 | Niemiec et al. |
| 9,271,846 B2 | 3/2016 | Lim et al. |
| 9,308,099 B2 | 4/2016 | Triplett et al. |
| 9,320,610 B2 | 4/2016 | Alheidt et al. |
| 9,351,845 B1 | 5/2016 | Pimenta et al. |
| 9,351,848 B2 | 5/2016 | Glerum et al. |
| 9,357,909 B2 | 6/2016 | Perez-Cruet et al. |
| 9,358,126 B2 | 6/2016 | Glerum et al. |
| 9,358,127 B2 | 6/2016 | Duffield et al. |
| 9,358,128 B2 | 6/2016 | Glerum et al. |
| 9,358,129 B2 | 6/2016 | Weiman |
| 9,364,341 B2 | 6/2016 | Gowan |
| 9,364,343 B2 | 6/2016 | Duffield et al. |
| 9,370,434 B2 | 6/2016 | Weiman |
| 9,370,435 B2 | 6/2016 | Walkenhorst et al. |
| 9,381,008 B2 | 7/2016 | Thornburg |
| 9,386,916 B2 | 7/2016 | Predick et al. |
| 9,387,092 B2 | 7/2016 | Mermuys et al. |
| 9,402,673 B2 | 8/2016 | Cormier et al. |
| 9,402,739 B2 | 8/2016 | Weiman et al. |
| 9,408,596 B2 | 8/2016 | Blain |
| 9,408,708 B2 | 8/2016 | Greenhalgh |
| 9,414,828 B2 | 8/2016 | Abidin et al. |
| 9,414,934 B2 | 8/2016 | Cain |
| 9,414,937 B2 | 8/2016 | Carlson et al. |
| 9,421,110 B2 | 8/2016 | Masson et al. |
| 9,427,331 B2 | 8/2016 | Arnin |
| 9,445,919 B2 | 9/2016 | Palmatier et al. |
| 9,452,063 B2 | 9/2016 | Glerum et al. |
| 9,456,903 B2 | 10/2016 | Glerum et al. |
| 9,456,906 B2 | 10/2016 | Gray et al. |

(56) References Cited

U.S. PATENT DOCUMENTS

| | | |
|---|---|---|
| 9,468,405 B2 | 10/2016 | Miles et al. |
| 9,474,622 B2 | 10/2016 | McLaughlin et al. |
| 9,474,625 B2 | 10/2016 | Weiman |
| 9,480,573 B2 | 11/2016 | Perloff et al. |
| 9,480,576 B2 | 11/2016 | Pepper et al. |
| 9,480,579 B2 | 11/2016 | Davenport et al. |
| 9,486,133 B2 | 11/2016 | Lee et al. |
| 9,486,325 B2 | 11/2016 | Davenport et al. |
| 9,486,327 B2 | 11/2016 | Martynova et al. |
| 9,486,328 B2 | 11/2016 | Jimenez et al. |
| 9,492,287 B2 | 11/2016 | Glerum et al. |
| 9,492,288 B2 | 11/2016 | Wagner et al. |
| 9,492,289 B2 | 11/2016 | Davenport et al. |
| 9,498,349 B2 | 11/2016 | Patterson et al. |
| 9,510,954 B2 | 12/2016 | Glerum et al. |
| 9,517,098 B2 | 12/2016 | Anderson |
| 9,522,070 B2 | 12/2016 | Flower et al. |
| 9,526,620 B2 | 12/2016 | Slivka et al. |
| 9,526,625 B2 | 12/2016 | Cain |
| 9,532,821 B2 | 1/2017 | Moskowitz et al. |
| 9,539,103 B2 | 1/2017 | McLaughlin et al. |
| 9,539,108 B2 | 1/2017 | Glerum et al. |
| 9,545,320 B2 | 1/2017 | Padovani et al. |
| 9,549,723 B2 | 1/2017 | Hynes et al. |
| 9,549,824 B2 | 1/2017 | McAfee |
| 9,561,116 B2 | 2/2017 | Weiman et al. |
| 9,566,163 B2 | 2/2017 | Suddaby et al. |
| 9,566,166 B2 | 2/2017 | Parry et al. |
| 9,566,168 B2 | 2/2017 | Glerum et al. |
| 9,572,560 B2 | 2/2017 | Mast et al. |
| 9,572,677 B2 | 2/2017 | Davenport et al. |
| 9,572,681 B2 | 2/2017 | Mathieu et al. |
| 9,579,124 B2 | 2/2017 | Gordon et al. |
| 9,579,139 B2 | 2/2017 | Cormier et al. |
| 9,579,213 B2 | 2/2017 | Bal et al. |
| 9,585,649 B2 | 3/2017 | Blain et al. |
| 9,585,762 B2 | 3/2017 | Suddaby et al. |
| 9,585,766 B2 | 3/2017 | Robinson |
| 9,585,767 B2 | 3/2017 | Robinson |
| 9,592,129 B2 | 3/2017 | Slivka et al. |
| 9,597,195 B2 | 3/2017 | Cain |
| 9,603,643 B2 | 3/2017 | Reed et al. |
| 9,603,713 B2 | 3/2017 | Moskowitz et al. |
| 9,603,717 B2 | 3/2017 | Ibarra et al. |
| 9,615,818 B2 | 4/2017 | Baudouin et al. |
| 9,615,936 B2 | 4/2017 | Duffield et al. |
| 9,622,732 B2 | 4/2017 | Martinelli et al. |
| 9,622,875 B2 | 4/2017 | Moskowitz et al. |
| 9,622,876 B1 | 4/2017 | Greenhalgh et al. |
| 9,629,729 B2 | 4/2017 | Grimberg, Jr. et al. |
| 9,636,097 B2 | 5/2017 | Bass |
| 9,642,720 B2 | 5/2017 | Radcliffe et al. |
| 9,649,198 B2 | 5/2017 | Wolters et al. |
| 9,655,746 B2 | 5/2017 | Seifert |
| 9,655,747 B2 | 5/2017 | Glerum et al. |
| 9,662,224 B2 | 5/2017 | Weiman et al. |
| 9,668,784 B2 | 6/2017 | Brumfield et al. |
| 9,668,876 B2 | 6/2017 | Blain et al. |
| 9,668,879 B2 | 6/2017 | Jimenez et al. |
| 9,675,465 B2 | 6/2017 | Padovani et al. |
| 9,675,467 B2 | 6/2017 | Duffield et al. |
| 9,675,468 B1 | 6/2017 | Jensen |
| 9,693,871 B2 | 7/2017 | Richerme et al. |
| 9,700,428 B2 | 7/2017 | Niemiec et al. |
| 9,707,092 B2 | 7/2017 | Davenport et al. |
| 9,713,536 B2 | 7/2017 | Foley et al. |
| 9,717,601 B2 | 8/2017 | Miller |
| 9,730,684 B2 | 8/2017 | Beale et al. |
| 9,730,806 B2 | 8/2017 | Capote |
| 9,737,288 B2 | 8/2017 | Karpowicz et al. |
| 9,750,617 B2 | 9/2017 | Lim et al. |
| 9,750,618 B1 | 9/2017 | Daffinson et al. |
| 9,757,249 B2 | 9/2017 | Radcliffe et al. |
| 9,763,722 B2 | 9/2017 | Roybal |
| 9,770,343 B2 | 9/2017 | Weiman |
| 9,782,265 B2 | 10/2017 | Weiman et al. |
| 9,788,971 B1 | 10/2017 | Stein |
| 9,795,370 B2 | 10/2017 | O'Connell et al. |
| 9,795,371 B2 | 10/2017 | Miles et al. |
| 9,801,733 B2 | 10/2017 | Wolters et al. |
| 9,801,734 B1 | 10/2017 | Stein et al. |
| 9,808,352 B2 | 11/2017 | Suddaby et al. |
| 9,826,966 B2 | 11/2017 | Mast et al. |
| 9,827,024 B2 | 11/2017 | Cormier et al. |
| 9,827,107 B1 | 11/2017 | Amin |
| 9,833,333 B2 | 12/2017 | Duffield et al. |
| 9,833,336 B2 | 12/2017 | Davenport et al. |
| 9,839,527 B2 | 12/2017 | Robinson |
| 9,839,528 B2 | 12/2017 | Weiman et al. |
| 9,848,993 B2 | 12/2017 | Moskowitz et al. |
| 9,848,996 B2 | 12/2017 | Faulhaber |
| 9,855,151 B2 | 1/2018 | Weiman |
| 9,867,715 B2 | 1/2018 | McLaughlin et al. |
| 9,872,779 B2 | 1/2018 | Miller et al. |
| 9,889,019 B2 | 2/2018 | Rogers et al. |
| 9,907,671 B2 | 3/2018 | Fessler |
| 9,907,673 B2 | 3/2018 | Weiman et al. |
| 9,918,709 B2 | 3/2018 | Sandhu |
| 9,924,859 B2 | 3/2018 | Lee et al. |
| 9,924,940 B2 | 3/2018 | Moskowitz et al. |
| 9,925,062 B2 | 3/2018 | Glerum et al. |
| 9,925,064 B2 | 3/2018 | Duffield et al. |
| 9,931,223 B2 | 4/2018 | Cain |
| 9,937,053 B2 | 4/2018 | Melkent et al. |
| 9,937,060 B2 | 4/2018 | Fuhrer et al. |
| 9,943,342 B2 | 4/2018 | Tanaka et al. |
| 9,943,418 B2 | 4/2018 | Davenport et al. |
| 9,949,775 B2 | 4/2018 | Reed et al. |
| 9,949,841 B2 | 4/2018 | Glerum et al. |
| 9,956,087 B2 | 5/2018 | Seifert et al. |
| 9,962,202 B2 | 5/2018 | Anderson |
| 9,962,270 B2 | 5/2018 | Alheidt et al. |
| 9,962,271 B2 | 5/2018 | Glerum |
| 9,962,272 B1 | 5/2018 | Daffinson et al. |
| 9,968,461 B2 | 5/2018 | Zappacosta et al. |
| 9,968,462 B2 | 5/2018 | Weiman |
| 9,974,531 B2 | 5/2018 | Miles et al. |
| 9,974,662 B2 | 5/2018 | Hessler et al. |
| 9,974,664 B2 | 5/2018 | Emerick et al. |
| 9,980,825 B2 | 5/2018 | Nichols et al. |
| 9,980,826 B2 | 5/2018 | Martynova et al. |
| 9,987,141 B2 | 6/2018 | Duffield et al. |
| 9,987,143 B2 | 6/2018 | Robinson et al. |
| 9,987,144 B2 | 6/2018 | Seifert et al. |
| 9,987,146 B1 | 6/2018 | Lentner et al. |
| 9,993,239 B2 | 6/2018 | Karpowicz et al. |
| 9,993,350 B2 | 6/2018 | Cain |
| 10,004,607 B2 | 6/2018 | Weiman et al. |
| 10,004,608 B2 | 6/2018 | Carnes et al. |
| 10,016,282 B2 | 7/2018 | Seifert et al. |
| 10,016,284 B2 | 7/2018 | Moskowitz et al. |
| 10,022,239 B1 | 7/2018 | Lentner et al. |
| 10,028,842 B2 | 7/2018 | Gray et al. |
| 10,034,765 B2 | 7/2018 | Blain et al. |
| 10,034,769 B2 | 7/2018 | Baynham |
| 10,034,771 B2 | 7/2018 | Capote et al. |
| 10,034,772 B2 | 7/2018 | Glerum et al. |
| 10,034,773 B2 | 7/2018 | McLaughlin et al. |
| 10,039,539 B2 | 8/2018 | Friedrich et al. |
| 10,039,650 B2 | 8/2018 | Lamborne et al. |
| 10,052,214 B2 | 8/2018 | Jimenez et al. |
| 10,058,431 B2 | 8/2018 | Tyber et al. |
| 10,060,469 B2 | 8/2018 | Jimenez et al. |
| 10,070,852 B2 | 9/2018 | Mast et al. |
| 10,076,320 B2 | 9/2018 | Mast et al. |
| 10,076,423 B2 | 9/2018 | Miller et al. |
| 10,080,666 B2 | 9/2018 | Suddaby et al. |
| 10,080,669 B2 | 9/2018 | Davenport et al. |
| 10,085,846 B2 | 10/2018 | Grotz |
| 10,085,849 B2 | 10/2018 | Weiman et al. |
| 10,092,417 B2 | 10/2018 | Weiman et al. |
| 10,098,758 B2 | 10/2018 | Matthews et al. |
| 10,098,759 B2 | 10/2018 | Weiman |
| 10,111,755 B2 | 10/2018 | Foley et al. |

(56) References Cited

U.S. PATENT DOCUMENTS

| | | |
|---|---|---|
| 10,111,758 B2 | 10/2018 | Robinson |
| 10,117,754 B2 | 11/2018 | Davenport et al. |
| 10,117,755 B2 | 11/2018 | Emerick et al. |
| 10,137,002 B2 | 11/2018 | Padovani et al. |
| 10,137,006 B2 | 11/2018 | Dewey et al. |
| 10,137,007 B2 | 11/2018 | Dewey et al. |
| 10,137,009 B2 | 11/2018 | Weiman et al. |
| 10,149,671 B2 | 12/2018 | Predick et al. |
| 10,149,710 B2 | 12/2018 | Tanaka et al. |
| 10,154,781 B2 | 12/2018 | Weiman |
| 10,154,912 B2 | 12/2018 | Glerum |
| 10,154,914 B2 | 12/2018 | Robinson |
| 10,159,584 B2 | 12/2018 | Carnes et al. |
| 10,166,117 B1 | 1/2019 | Daffinson et al. |
| 10,172,515 B2 | 1/2019 | Lee et al. |
| 10,172,652 B2 | 1/2019 | Woolley et al. |
| 10,178,987 B2 | 1/2019 | Predick et al. |
| 10,179,053 B2 | 1/2019 | Zappacosta et al. |
| 10,182,922 B2 | 1/2019 | Nichols et al. |
| 10,188,527 B2 | 1/2019 | Rogers et al. |
| 10,195,050 B2 | 2/2019 | Palmatier et al. |
| 10,201,431 B2 | 2/2019 | Slater et al. |
| 10,213,192 B2 | 2/2019 | Capote |
| 10,213,193 B2 | 2/2019 | Karpowicz et al. |
| 10,219,798 B2 | 3/2019 | Capote |
| 10,219,913 B2 | 3/2019 | Matthews et al. |
| 10,219,914 B2 | 3/2019 | Faulhaber |
| 10,219,915 B1 | 3/2019 | Stein |
| 10,226,356 B2 | 3/2019 | Grotz |
| 10,226,359 B2 | 3/2019 | Glerum et al. |
| 10,238,375 B2 | 3/2019 | O'Connell et al. |
| 10,238,383 B2 | 3/2019 | Moskowitz et al. |
| 10,238,503 B2 | 3/2019 | Branch et al. |
| 10,245,015 B2 | 4/2019 | Predick et al. |
| 10,251,643 B2 | 4/2019 | Moskowitz et al. |
| 10,265,191 B2 | 4/2019 | Lim et al. |
| 10,278,686 B2 | 5/2019 | Baudouin et al. |
| 10,278,786 B2 | 5/2019 | Friedrich et al. |
| 10,278,830 B1 | 5/2019 | Walker et al. |
| 10,278,831 B2 | 5/2019 | Sandul |
| 10,278,832 B2 | 5/2019 | Nichols et al. |
| 10,285,680 B2 | 5/2019 | Friedrich et al. |
| 10,285,819 B2 | 5/2019 | Greenhalgh |
| 10,285,824 B2 | 5/2019 | Robinson |
| 10,292,828 B2 | 5/2019 | Greenhalgh |
| 10,299,777 B2 | 5/2019 | Mast et al. |
| 10,299,934 B2 | 5/2019 | Seifert et al. |
| 10,299,937 B2 | 5/2019 | McAfee |
| 10,307,268 B2 | 6/2019 | Moskowitz et al. |
| 10,314,622 B2 | 6/2019 | Brumfield et al. |
| 10,314,719 B2 | 6/2019 | Hessler et al. |
| 10,322,007 B2 | 6/2019 | Masson et al. |
| 10,322,009 B2 | 6/2019 | Aghayev et al. |
| 10,327,909 B2 | 6/2019 | Baynham |
| 10,327,912 B1 | 6/2019 | Suddaby |
| 10,327,917 B2 | 6/2019 | Glerum et al. |
| 10,342,675 B2 | 7/2019 | Alheidt |
| 10,350,085 B2 | 7/2019 | Glerum et al. |
| 10,357,233 B2 | 7/2019 | Miles et al. |
| 10,363,142 B2 | 7/2019 | McClintock et al. |
| 10,363,144 B2 | 7/2019 | Overes et al. |
| 10,369,004 B2 | 8/2019 | Faulhaber |
| 10,369,008 B2 | 8/2019 | Jimenez et al. |
| 10,369,010 B2 | 8/2019 | Robinson et al. |
| 10,369,012 B2 | 8/2019 | Fessler |
| 10,376,377 B2 | 8/2019 | Seifert et al. |
| 10,390,962 B2 | 8/2019 | Weiman |
| 10,390,964 B2 | 8/2019 | Faulhaber |
| 10,398,563 B2 | 9/2019 | Engstrom |
| 10,398,566 B2 | 9/2019 | Olmos et al. |
| 10,413,419 B2 | 9/2019 | Thibodeau |
| 10,413,422 B2 | 9/2019 | Flower et al. |
| 10,413,423 B2 | 9/2019 | Overes et al. |
| 10,426,450 B2 | 10/2019 | Vogel et al. |
| 10,426,633 B2 | 10/2019 | Moskowitz et al. |
| 10,426,634 B1 | 10/2019 | Al-Jazaeri et al. |
| 10,441,430 B2 | 10/2019 | Ludwig et al. |
| 10,449,056 B2 | 10/2019 | Cain |
| 10,456,122 B2 | 10/2019 | Koltz et al. |
| 10,470,894 B2 | 11/2019 | Foley et al. |
| 10,478,319 B2 | 11/2019 | Moskowitz et al. |
| 10,492,912 B2 | 12/2019 | Gregersen et al. |
| 10,492,922 B2 | 12/2019 | Mathieu et al. |
| 10,492,924 B2 | 12/2019 | Stein et al. |
| 10,500,064 B2 | 12/2019 | Robinson |
| 10,512,550 B2 | 12/2019 | Bechtel et al. |
| 10,517,645 B2 | 12/2019 | van der Pol |
| 10,524,924 B2 | 1/2020 | Davenport et al. |
| 10,531,903 B2 | 1/2020 | Daly et al. |
| 10,537,436 B2 | 1/2020 | Maguire et al. |
| 10,537,438 B2 | 1/2020 | Martynova et al. |
| 10,555,729 B1 | 2/2020 | Cole et al. |
| 10,561,411 B1 | 2/2020 | Cole et al. |
| 10,575,889 B2 | 3/2020 | Roybal |
| 10,575,960 B2 | 3/2020 | Duffield et al. |
| 10,582,959 B2 | 3/2020 | Langer et al. |
| 10,583,015 B2 | 3/2020 | Olmos et al. |
| 10,603,078 B2 | 3/2020 | Simpson et al. |
| 10,610,376 B2 | 4/2020 | Kuyler et al. |
| 10,624,757 B2 | 4/2020 | Bost et al. |
| 10,624,758 B2 | 4/2020 | Slivka et al. |
| 10,624,761 B2 | 4/2020 | Davenport et al. |
| 10,639,163 B2 | 5/2020 | Tyber et al. |
| 10,639,166 B2 | 5/2020 | Weiman et al. |
| 10,653,458 B2 | 5/2020 | Tanaka et al. |
| 10,667,925 B2 | 6/2020 | Emerick et al. |
| 10,667,927 B2 | 6/2020 | Lamborne et al. |
| 10,675,157 B2 | 6/2020 | Zakelj et al. |
| 10,682,241 B2 | 6/2020 | Glerum et al. |
| 10,687,963 B2 | 6/2020 | Jimenez et al. |
| 10,702,393 B2 | 7/2020 | Davenport et al. |
| 10,709,569 B2 | 7/2020 | McLaughlin et al. |
| 10,709,571 B2 | 7/2020 | Iott et al. |
| 10,709,572 B2 | 7/2020 | Daffinson et al. |
| 10,709,575 B2 | 7/2020 | Robinson |
| 10,722,377 B2 | 7/2020 | Glerum et al. |
| 10,722,379 B2 | 7/2020 | McLaughlin et al. |
| 10,729,561 B2 | 8/2020 | Glerum |
| 10,743,858 B1 | 8/2020 | Cole et al. |
| 10,744,002 B2 | 8/2020 | Glerum et al. |
| 10,758,366 B2 | 9/2020 | Daffinson et al. |
| 10,758,367 B2 | 9/2020 | Weiman et al. |
| 10,758,369 B2 | 9/2020 | Rogers et al. |
| 10,765,528 B2 | 9/2020 | Weiman et al. |
| 10,772,737 B2 | 9/2020 | Gray et al. |
| 10,779,955 B2 | 9/2020 | Kuyler et al. |
| 10,779,957 B2 | 9/2020 | Weiman et al. |
| 10,786,364 B2 | 9/2020 | Davenport et al. |
| 10,786,369 B2 | 9/2020 | Carnes et al. |
| 10,799,368 B2 | 10/2020 | Glerum et al. |
| 10,835,387 B2 | 11/2020 | Weiman et al. |
| 10,842,640 B2 | 11/2020 | Weiman et al. |
| 10,842,644 B2 | 11/2020 | Weiman et al. |
| 10,856,997 B2 | 12/2020 | Cowan et al. |
| 10,869,769 B2 | 12/2020 | Eisen et al. |
| 10,874,447 B2 | 12/2020 | Tanaka et al. |
| 10,874,522 B2 | 12/2020 | Weiman |
| 10,874,523 B2 | 12/2020 | Weiman et al. |
| 10,874,524 B2 | 12/2020 | Bjork |
| 10,881,524 B2 | 1/2021 | Eisen et al. |
| 10,881,531 B2 | 1/2021 | Berry |
| 10,888,431 B1 | 1/2021 | Robinson |
| 10,898,344 B2 | 1/2021 | Alheidt et al. |
| 10,898,346 B1 | 1/2021 | Suddaby |
| 10,925,656 B2 | 2/2021 | Cole et al. |
| 10,925,750 B2 | 2/2021 | Zappacosta et al. |
| 10,925,752 B2 | 2/2021 | Weiman |
| 10,932,920 B2 | 3/2021 | Dewey et al. |
| 10,940,014 B2 | 3/2021 | Greenhalgh |
| 10,945,858 B2 | 3/2021 | Bechtel et al. |
| 10,952,866 B2 | 3/2021 | Warren et al. |
| 10,959,855 B2 | 3/2021 | Miller et al. |
| 10,959,856 B2 | 3/2021 | Seifert et al. |
| 10,973,649 B2 | 4/2021 | Weiman et al. |

(56) References Cited

U.S. PATENT DOCUMENTS

| | | |
|---|---|---|
| 10,973,650 B2 | 4/2021 | Stein |
| 10,980,642 B2 | 4/2021 | Glerum et al. |
| 10,980,644 B2 | 4/2021 | Purcell et al. |
| 10,993,814 B2 | 5/2021 | Wolters |
| 11,007,067 B2 | 5/2021 | Masson et al. |
| 11,013,617 B2 | 5/2021 | Weiman et al. |
| 11,020,238 B2 | 6/2021 | Nichols et al. |
| 11,020,239 B2 | 6/2021 | Miller et al. |
| 11,026,804 B2 | 6/2021 | Jimenez et al. |
| 11,026,812 B2 | 6/2021 | Daffinson et al. |
| 11,033,401 B2 | 6/2021 | Shoshtaev |
| 11,033,402 B2 | 6/2021 | Melkent et al. |
| 11,033,404 B2 | 6/2021 | Faulhaber |
| 11,039,935 B2 | 6/2021 | McAfee |
| 11,045,326 B2 | 6/2021 | Seifert et al. |
| 11,045,327 B2 | 6/2021 | Nichols et al. |
| 11,051,949 B2 | 7/2021 | Walker et al. |
| 11,051,951 B2 | 7/2021 | Robinson et al. |
| 11,058,469 B2 | 7/2021 | Mahajan et al. |
| 11,065,127 B1 | 7/2021 | Lentner et al. |
| 11,065,129 B2 | 7/2021 | Sandul |
| 11,065,130 B2 | 7/2021 | Branch et al. |
| 11,076,966 B2 | 8/2021 | Faulhaber |
| 11,083,584 B2 | 8/2021 | Lauf et al. |
| 11,083,595 B2 | 8/2021 | Robinson |
| 11,090,167 B2 | 8/2021 | Emerick et al. |
| 11,096,795 B2 | 8/2021 | Padovani et al. |
| 11,096,797 B2 | 8/2021 | Moskowitz et al. |
| 11,103,366 B2 | 8/2021 | Glerum et al. |
| RE48,719 E | 9/2021 | Suddaby et al. |
| 11,109,980 B2 | 9/2021 | Seifert et al. |
| 11,116,644 B2 | 9/2021 | Marrocco et al. |
| 11,123,198 B2 | 9/2021 | Black et al. |
| 11,123,200 B2 | 9/2021 | Faulhaber |
| 11,129,731 B2 | 9/2021 | Miller et al. |
| 11,135,071 B2 | 10/2021 | Dewey et al. |
| 11,147,680 B2 | 10/2021 | Tyber et al. |
| 11,154,404 B2 | 10/2021 | Freedman et al. |
| 11,160,666 B2 | 11/2021 | Burkhardt et al. |
| 11,160,669 B2 | 11/2021 | Rogers et al. |
| 11,166,826 B2 | 11/2021 | Huang |
| 11,173,044 B1 | 11/2021 | Jones et al. |
| 11,179,234 B2 | 11/2021 | Dacosta et al. |
| 11,285,014 B1 | 3/2022 | Josse et al. |
| 11,376,134 B1 | 7/2022 | Dewey et al. |
| 11,617,658 B2 | 4/2023 | Josse et al. |
| 11,723,780 B2 | 8/2023 | Seifert et al. |
| 11,737,892 B1 | 8/2023 | Kadaba et al. |
| 12,064,354 B2 | 8/2024 | Robinson et al. |
| 2002/0045943 A1 | 4/2002 | Uk |
| 2002/0045945 A1 | 4/2002 | Liu et al. |
| 2002/0055741 A1 | 5/2002 | Schlapfer et al. |
| 2002/0116066 A1 | 8/2002 | Chauvin et al. |
| 2002/0128713 A1 | 9/2002 | Ferree |
| 2002/0151976 A1 | 10/2002 | Foley et al. |
| 2002/0183762 A1 | 12/2002 | Anderson et al. |
| 2003/0050701 A1 | 3/2003 | Michelson |
| 2003/0130739 A1 | 7/2003 | Gerbec et al. |
| 2003/0163132 A1 | 8/2003 | Chin |
| 2004/0102778 A1 | 5/2004 | Huebner et al. |
| 2004/0172134 A1 | 9/2004 | Berry |
| 2004/0186570 A1 | 9/2004 | Rapp |
| 2004/0193158 A1 | 9/2004 | Lim et al. |
| 2004/0204713 A1 | 10/2004 | Abdou |
| 2004/0249461 A1 | 12/2004 | Ferree |
| 2004/0254643 A1 | 12/2004 | Jackson |
| 2004/0254644 A1 | 12/2004 | Taylor |
| 2005/0015149 A1 | 1/2005 | Michelson |
| 2005/0033429 A1 | 2/2005 | Kuo |
| 2005/0033439 A1 | 2/2005 | Gordon et al. |
| 2005/0147478 A1 | 7/2005 | Greenberg |
| 2005/0154459 A1* | 7/2005 | Wolek ............... A61F 2/44 623/17.11 |
| 2005/0209698 A1 | 9/2005 | Gordon et al. |
| 2005/0228398 A1 | 10/2005 | Rathbun et al. |
| 2006/0122701 A1 | 6/2006 | Kiester |
| 2006/0129244 A1 | 6/2006 | Ensign |
| 2006/0260446 A1 | 11/2006 | Chang |
| 2006/0276901 A1 | 12/2006 | Zipnick et al. |
| 2007/0173840 A1 | 7/2007 | Huebner |
| 2007/0218750 A1 | 9/2007 | Corrao et al. |
| 2007/0233150 A1 | 10/2007 | Blain et al. |
| 2007/0270859 A1 | 11/2007 | Companioni et al. |
| 2008/0058804 A1 | 3/2008 | Lechot et al. |
| 2008/0132959 A1 | 6/2008 | Mikkonen et al. |
| 2008/0140207 A1 | 6/2008 | Olmos et al. |
| 2009/0024158 A1 | 1/2009 | Viker |
| 2009/0093830 A1 | 4/2009 | Miller |
| 2009/0105834 A1* | 4/2009 | Hovda ............... A61F 2/30771 623/17.11 |
| 2009/0292361 A1 | 11/2009 | Lopez |
| 2010/0070035 A1 | 3/2010 | Mayer |
| 2010/0076440 A1 | 3/2010 | Pamichev et al. |
| 2010/0082109 A1 | 4/2010 | Greenhalgh et al. |
| 2010/0152853 A1 | 6/2010 | Kirschman |
| 2010/0191336 A1 | 7/2010 | Greenhalgh |
| 2010/0211176 A1 | 8/2010 | Greenhalgh |
| 2010/0280617 A1 | 11/2010 | Coppes et al. |
| 2010/0286777 A1 | 11/2010 | Errico et al. |
| 2011/0118843 A1 | 5/2011 | Mathieu et al. |
| 2011/0130838 A1 | 6/2011 | Morgenstern Lopez |
| 2011/0153020 A1 | 6/2011 | Abdelgany et al. |
| 2011/0218572 A1 | 9/2011 | Lechmann et al. |
| 2011/0218631 A1 | 9/2011 | Woodburn, Sr. et al. |
| 2011/0301577 A1 | 12/2011 | Simmen et al. |
| 2012/0004732 A1 | 1/2012 | Goel et al. |
| 2012/0095515 A1 | 4/2012 | Hamilton |
| 2012/0101581 A1 | 4/2012 | Mathieu et al. |
| 2012/0109142 A1 | 5/2012 | Dayan |
| 2012/0109309 A1 | 5/2012 | Mathieu et al. |
| 2012/0109310 A1 | 5/2012 | Mathieu et al. |
| 2012/0109312 A1 | 5/2012 | Mathieu et al. |
| 2012/0109313 A1 | 5/2012 | Mathieu et al. |
| 2012/0123546 A1 | 5/2012 | Medina |
| 2012/0143195 A1 | 6/2012 | Sander |
| 2012/0150237 A1 | 6/2012 | Combrowski |
| 2012/0197401 A1 | 8/2012 | Duncan et al. |
| 2012/0209385 A1 | 8/2012 | Aferzon |
| 2012/0215313 A1 | 8/2012 | Saidha et al. |
| 2012/0215316 A1 | 8/2012 | Mohr et al. |
| 2013/0103095 A1 | 4/2013 | Brumfield et al. |
| 2013/0158664 A1 | 6/2013 | Palmatier et al. |
| 2013/0184823 A1 | 7/2013 | Malberg |
| 2013/0190876 A1 | 7/2013 | Drochner et al. |
| 2013/0211526 A1 | 8/2013 | Alheidt et al. |
| 2013/0226191 A1 | 8/2013 | Thoren et al. |
| 2013/0231747 A1 | 9/2013 | Olmos et al. |
| 2013/0274557 A1 | 10/2013 | Bowman et al. |
| 2013/0304136 A1 | 11/2013 | Gourlaouen-Preissler et al. |
| 2013/0317312 A1 | 11/2013 | Eastlack et al. |
| 2014/0018816 A1 | 1/2014 | Fenn et al. |
| 2014/0107790 A1 | 4/2014 | Combrowski |
| 2014/0114321 A1 | 4/2014 | Davenport et al. |
| 2014/0114420 A1 | 4/2014 | Robinson |
| 2014/0148904 A1 | 5/2014 | Robinson |
| 2014/0163682 A1 | 6/2014 | Iott et al. |
| 2014/0180419 A1 | 6/2014 | Dmuschewsky |
| 2014/0194992 A1 | 7/2014 | Medina |
| 2014/0249629 A1 | 9/2014 | Moskowitz et al. |
| 2014/0249631 A1 | 9/2014 | Weiman |
| 2014/0277471 A1 | 9/2014 | Gray et al. |
| 2014/0277473 A1 | 9/2014 | Perrow |
| 2014/0277487 A1 | 9/2014 | Davenport et al. |
| 2014/0277500 A1 | 9/2014 | Logan et al. |
| 2014/0303674 A1 | 10/2014 | Sasing |
| 2014/0364855 A1 | 12/2014 | Stoll et al. |
| 2015/0173915 A1 | 6/2015 | Laubert et al. |
| 2015/0223945 A1 | 8/2015 | Weiman et al. |
| 2015/0230931 A1 | 8/2015 | Greenhalgh |
| 2015/0238236 A1 | 8/2015 | Sasing |
| 2015/0354635 A1 | 12/2015 | McClymont et al. |
| 2015/0374507 A1 | 12/2015 | Wolters et al. |
| 2016/0008924 A1 | 1/2016 | Canourgues et al. |
| 2016/0022434 A1 | 1/2016 | Robinson |

(56) References Cited

U.S. PATENT DOCUMENTS

| | | |
|---|---|---|
| 2016/0051373 A1 | 2/2016 | Faulhaber |
| 2016/0058571 A1 | 3/2016 | McLaughlin et al. |
| 2016/0081681 A1 | 3/2016 | Waugh et al. |
| 2016/0089247 A1 | 3/2016 | Nichols et al. |
| 2016/0095710 A1 | 4/2016 | Juszczyk et al. |
| 2016/0095718 A1 | 4/2016 | Burkhardt et al. |
| 2016/0100951 A1 | 4/2016 | Suddaby et al. |
| 2016/0128847 A1 | 5/2016 | Kurtaliaj et al. |
| 2016/0199073 A1 | 7/2016 | Nino et al. |
| 2016/0242930 A1 | 8/2016 | Duffield et al. |
| 2016/0256291 A1 | 9/2016 | Miller |
| 2016/0278830 A1 | 9/2016 | Arrington |
| 2016/0296340 A1 | 10/2016 | Gordon et al. |
| 2016/0310291 A1 | 10/2016 | Greenhalgh |
| 2016/0345952 A1 | 12/2016 | Kucharzyk et al. |
| 2016/0367377 A1 | 12/2016 | Faulhaber |
| 2017/0010025 A1 | 1/2017 | Mayershofer |
| 2017/0029635 A1 | 2/2017 | Doll et al. |
| 2017/0035406 A1 | 2/2017 | Abidin et al. |
| 2017/0049651 A1 | 2/2017 | Lim et al. |
| 2017/0049653 A1 | 2/2017 | Lim et al. |
| 2017/0095345 A1 | 4/2017 | Davenport et al. |
| 2017/0100255 A1 | 4/2017 | Hleihil et al. |
| 2017/0100257 A1 | 4/2017 | Weiman et al. |
| 2017/0105844 A1 | 4/2017 | Kuyler et al. |
| 2017/0112630 A1 | 4/2017 | Kuyler et al. |
| 2017/0151065 A1 | 6/2017 | Warren et al. |
| 2017/0156882 A1 | 6/2017 | Rathbun et al. |
| 2017/0156884 A1 | 6/2017 | Rathbun et al. |
| 2017/0189200 A1 | 7/2017 | Miller et al. |
| 2017/0189204 A1 | 7/2017 | Riemhofer et al. |
| 2017/0202678 A1 | 7/2017 | Duffield et al. |
| 2017/0215856 A1 | 8/2017 | Martinelli et al. |
| 2017/0224502 A1 | 8/2017 | Wolters et al. |
| 2017/0224504 A1 | 8/2017 | Butler et al. |
| 2017/0231675 A1 | 8/2017 | Combrowski |
| 2017/0231780 A1 | 8/2017 | D'Urso |
| 2017/0246006 A1 | 8/2017 | Carnes et al. |
| 2017/0290677 A1 | 10/2017 | Olmos et al. |
| 2017/0296352 A1 | 10/2017 | Richerme et al. |
| 2017/0333200 A1 | 11/2017 | Arnin |
| 2017/0367842 A1 | 12/2017 | Predick et al. |
| 2017/0367843 A1 | 12/2017 | Eisen et al. |
| 2017/0367844 A1 | 12/2017 | Eisen et al. |
| 2017/0367845 A1 | 12/2017 | Eisen et al. |
| 2018/0000606 A1 | 1/2018 | Hessler et al. |
| 2018/0030362 A1 | 2/2018 | Kosler et al. |
| 2018/0031810 A1 | 2/2018 | Hsu et al. |
| 2018/0036136 A1 | 2/2018 | Duffield et al. |
| 2018/0036138 A1 | 2/2018 | Robinson |
| 2018/0104066 A1 | 4/2018 | Bae et al. |
| 2018/0116819 A1 | 5/2018 | Maguire et al. |
| 2018/0116891 A1 | 5/2018 | Beale et al. |
| 2018/0193160 A1 | 7/2018 | Hsu et al. |
| 2018/0193164 A1 | 7/2018 | Shoshtaev |
| 2018/0206999 A1 | 7/2018 | Suddaby |
| 2018/0256356 A1 | 9/2018 | Robinson et al. |
| 2018/0256359 A1 | 9/2018 | Greenhalgh |
| 2018/0256360 A1 | 9/2018 | Cain |
| 2018/0256362 A1 | 9/2018 | Slivka et al. |
| 2018/0263784 A1 | 9/2018 | Bechtel et al. |
| 2018/0271513 A1 | 9/2018 | Perrow et al. |
| 2018/0280142 A1 | 10/2018 | Schultz et al. |
| 2018/0303473 A1 | 10/2018 | Spann et al. |
| 2018/0303621 A1 | 10/2018 | Brotman et al. |
| 2018/0303625 A1 | 10/2018 | Alheidt et al. |
| 2018/0311048 A1 | 11/2018 | Glerum et al. |
| 2018/0318101 A1 | 11/2018 | Engstrom |
| 2018/0318102 A1 | 11/2018 | Seifert et al. |
| 2018/0325574 A1 | 11/2018 | Bjork et al. |
| 2018/0338838 A1 | 11/2018 | Cryder et al. |
| 2018/0338841 A1 | 11/2018 | Miller et al. |
| 2018/0344307 A1 | 12/2018 | Hynes et al. |
| 2018/0360616 A1 | 12/2018 | Luu |
| 2019/0000640 A1 | 1/2019 | Weiman |
| 2019/0000702 A1 | 1/2019 | Lim et al. |
| 2019/0000707 A1 | 1/2019 | Lim et al. |
| 2019/0020121 A1 | 1/2019 | Paulotto et al. |
| 2019/0021716 A1 | 1/2019 | Waugh et al. |
| 2019/0021873 A1 | 1/2019 | Dmuschewsky |
| 2019/0046329 A1 | 2/2019 | Padovani et al. |
| 2019/0046381 A1 | 2/2019 | Lim et al. |
| 2019/0046383 A1 | 2/2019 | Lim et al. |
| 2019/0060083 A1 | 2/2019 | Weiman et al. |
| 2019/0082949 A1 | 3/2019 | Weiman |
| 2019/0083081 A1 | 3/2019 | Ortiz et al. |
| 2019/0091033 A1 | 3/2019 | Dewey et al. |
| 2019/0105175 A1 | 4/2019 | Zappacosta et al. |
| 2019/0125328 A1 | 5/2019 | Blain |
| 2019/0133434 A1 | 5/2019 | Lee et al. |
| 2019/0133645 A1 | 5/2019 | Gordon et al. |
| 2019/0133779 A1 | 5/2019 | McLaughlin et al. |
| 2019/0133780 A1 | 5/2019 | Matthews et al. |
| 2019/0133784 A1 | 5/2019 | Gunn et al. |
| 2019/0133788 A1 | 5/2019 | Weiman et al. |
| 2019/0142480 A1 | 5/2019 | Woolley et al. |
| 2019/0151115 A1 | 5/2019 | Nichols et al. |
| 2019/0183656 A1 | 6/2019 | Stein |
| 2019/0201209 A1 | 7/2019 | Branch et al. |
| 2019/0201210 A1 | 7/2019 | Besaw et al. |
| 2019/0209155 A1 | 7/2019 | Mast et al. |
| 2019/0216453 A1 | 7/2019 | Predick et al. |
| 2019/0231552 A1 | 8/2019 | Sandul |
| 2019/0240039 A1 | 8/2019 | Walker et al. |
| 2019/0240043 A1 | 8/2019 | Greenhalgh |
| 2019/0247098 A1 | 8/2019 | Brumfield et al. |
| 2019/0254650 A1 | 8/2019 | Martinelli et al. |
| 2019/0254838 A1 | 8/2019 | Miller et al. |
| 2019/0254839 A1 | 8/2019 | Nichols et al. |
| 2019/0262009 A1 | 8/2019 | Cheng |
| 2019/0262139 A1 | 8/2019 | Wolters |
| 2019/0269521 A1 | 9/2019 | Shoshtaev |
| 2019/0274670 A1 | 9/2019 | O'Connell et al. |
| 2019/0274671 A1 | 9/2019 | Lauf et al. |
| 2019/0274836 A1 | 9/2019 | Eisen et al. |
| 2019/0282373 A1 | 9/2019 | Alheidt |
| 2019/0290446 A1 | 9/2019 | Masson et al. |
| 2019/0290447 A1 | 9/2019 | Stein |
| 2019/0298416 A1 | 10/2019 | Rezach |
| 2019/0298524 A1 | 10/2019 | Lauf et al. |
| 2019/0298540 A1 | 10/2019 | Aghayev et al. |
| 2019/0321022 A1 | 10/2019 | Karpowicz et al. |
| 2019/0321190 A1 | 10/2019 | Wagner et al. |
| 2019/0328539 A1 | 10/2019 | Suh et al. |
| 2019/0328540 A1 | 10/2019 | Seifert et al. |
| 2019/0329388 A1 | 10/2019 | Erickson et al. |
| 2019/0336301 A1 | 11/2019 | Engstrom |
| 2019/0336304 A1 | 11/2019 | Burkhardt et al. |
| 2019/0350573 A1 | 11/2019 | Vogel et al. |
| 2019/0358049 A1 | 11/2019 | Faulhaber |
| 2019/0358050 A1 | 11/2019 | Fessler |
| 2019/0358051 A1 | 11/2019 | Flower et al. |
| 2019/0380840 A1 | 12/2019 | Tyber et al. |
| 2019/0388232 A1 | 12/2019 | Purcell et al. |
| 2020/0008951 A1 | 1/2020 | McClintock et al. |
| 2020/0030114 A1 | 1/2020 | Cain |
| 2020/0030116 A1 | 1/2020 | Jimenez et al. |
| 2020/0038200 A1 | 2/2020 | Foley et al. |
| 2020/0054461 A1 | 2/2020 | Marrocco et al. |
| 2020/0060844 A1 | 2/2020 | Mathieu et al. |
| 2020/0069316 A1 | 3/2020 | DeSoutter et al. |
| 2020/0078190 A1 | 3/2020 | Rogers et al. |
| 2020/0093526 A1 | 3/2020 | Daly et al. |
| 2020/0093607 A1 | 3/2020 | Davenport et al. |
| 2020/0093609 A1 | 3/2020 | Shoshtaev |
| 2020/0100904 A1 | 4/2020 | Stein et al. |
| 2020/0107824 A1 | 4/2020 | Fleischer |
| 2020/0129306 A1 | 4/2020 | Miller et al. |
| 2020/0129307 A1 | 4/2020 | Hunziker et al. |
| 2020/0138591 A1 | 5/2020 | Moskowitz et al. |
| 2020/0138593 A1 | 5/2020 | Martynova et al. |
| 2020/0146840 A1 | 5/2020 | Black et al. |
| 2020/0179120 A1 | 6/2020 | Bielenstein et al. |
| 2020/0205993 A1 | 7/2020 | Davenport et al. |

(56) References Cited

U.S. PATENT DOCUMENTS

| | | |
|---|---|---|
| 2020/0214754 A1 | 7/2020 | Bowen et al. |
| 2020/0222202 A1 | 7/2020 | Kuyler et al. |
| 2020/0229944 A1 | 7/2020 | Suh et al. |
| 2020/0246159 A1 | 8/2020 | Suh et al. |
| 2020/0246162 A1 | 8/2020 | Schultz et al. |
| 2020/0261242 A1 | 8/2020 | Bost et al. |
| 2020/0268524 A1 | 8/2020 | Glerum et al. |
| 2020/0276028 A1 | 9/2020 | Blain et al. |
| 2020/0281741 A1 | 9/2020 | Grotz |
| 2020/0289287 A1 | 9/2020 | Emerick et al. |
| 2020/0297507 A1 | 9/2020 | Iott et al. |
| 2020/0330239 A1 | 10/2020 | Davenport et al. |
| 2020/0330245 A1 | 10/2020 | Glerum |
| 2020/0345511 A1 | 11/2020 | Daffinson et al. |
| 2020/0352731 A1 | 11/2020 | Berry |
| 2020/0352738 A1 | 11/2020 | Berry |
| 2020/0360153 A1 | 11/2020 | Weiman et al. |
| 2020/0375753 A1 | 12/2020 | McLaughlin et al. |
| 2020/0375755 A1 | 12/2020 | Cain |
| 2020/0383797 A1 | 12/2020 | Predick et al. |
| 2020/0383799 A1 | 12/2020 | Cain |
| 2020/0390433 A1 | 12/2020 | Yu et al. |
| 2020/0390565 A1 | 12/2020 | Jimenez et al. |
| 2020/0397593 A1 | 12/2020 | Davenport et al. |
| 2020/0405497 A1 | 12/2020 | Olmos et al. |
| 2020/0405498 A1 | 12/2020 | Gray et al. |
| 2020/0405499 A1 | 12/2020 | Gerbec et al. |
| 2020/0405500 A1 | 12/2020 | Cain |
| 2021/0007860 A1 | 1/2021 | Glerum et al. |
| 2021/0015626 A1 | 1/2021 | Suddaby |
| 2021/0030555 A1 | 2/2021 | Weiman et al. |
| 2021/0030561 A1 | 2/2021 | Gleason |
| 2021/0045891 A1 | 2/2021 | Rogers et al. |
| 2021/0045892 A1 | 2/2021 | Rogers et al. |
| 2021/0052395 A1 | 2/2021 | Iott et al. |
| 2021/0068959 A1 | 3/2021 | McLuen et al. |
| 2021/0068974 A1 | 3/2021 | Cowan et al. |
| 2021/0068982 A1 | 3/2021 | Carnes et al. |
| 2021/0077271 A1 | 3/2021 | Sharabani |
| 2021/0077272 A1 | 3/2021 | Eisen et al. |
| 2021/0085479 A1 | 3/2021 | Weiman et al. |
| 2021/0093462 A1 | 4/2021 | Lucasiewicz et al. |
| 2021/0106434 A1 | 4/2021 | Alheidt et al. |
| 2021/0113349 A1 | 4/2021 | Weiman et al. |
| 2021/0121299 A1 | 4/2021 | Hyder |
| 2021/0121300 A1 | 4/2021 | Weiman et al. |
| 2021/0137697 A1 | 5/2021 | Weiman |
| 2021/0137699 A1 | 5/2021 | Jang et al. |
| 2021/0137701 A1 | 5/2021 | Miller et al. |
| 2021/0154811 A1 | 5/2021 | Spreiter et al. |
| 2021/0161678 A1 | 6/2021 | Dewey et al. |
| 2021/0177618 A1 | 6/2021 | Branch et al. |
| 2021/0186706 A1 | 6/2021 | Spitler et al. |
| 2021/0186709 A1 | 6/2021 | Weiman et al. |
| 2021/0196470 A1 | 7/2021 | Shoshtaev |
| 2021/0205092 A1 | 7/2021 | Glerum et al. |
| 2021/0205094 A1 | 7/2021 | Neiman et al. |
| 2021/0220145 A1 | 7/2021 | Stein |
| 2021/0220147 A1 | 7/2021 | Berry |
| 2021/0236298 A1 | 8/2021 | Weiman et al. |
| 2021/0251770 A1 | 8/2021 | Purcell et al. |
| 2021/0251776 A1 | 8/2021 | Daffinson et al. |
| 2021/0259848 A1 | 8/2021 | Kang et al. |
| 2021/0259849 A1 | 8/2021 | Robinson et al. |
| 2021/0259850 A1 | 8/2021 | Eisen et al. |
| 2021/0267767 A1 | 9/2021 | Stein |
| 2021/0275317 A1 | 9/2021 | Spetzger |
| 2021/0275318 A1 | 9/2021 | Reimels |
| 2021/0275319 A1 | 9/2021 | Reimels |
| 2021/0275321 A1 | 9/2021 | Seifert et al. |
| 2021/0282938 A1 | 9/2021 | Nichols et al. |
| 2021/0298915 A1 | 9/2021 | Faulhaber |
| 2021/0298916 A1 | 9/2021 | Melkent et al. |
| 2021/0307920 A1 | 10/2021 | Walker et al. |
| 2021/0315705 A1 | 10/2021 | Altarac et al. |
| 2021/0322179 A1 | 10/2021 | Miller et al. |
| 2021/0322181 A1 | 10/2021 | Predick |
| 2021/0322182 A1 | 10/2021 | Faulhaber |
| 2021/0330472 A1 | 10/2021 | Shoshtaev |
| 2021/0346174 A1 | 11/2021 | Flint et al. |
| 2021/0401586 A1 | 12/2021 | Zakelj |
| 2022/0015924 A1 | 1/2022 | Freedman et al. |
| 2022/0047312 A1 | 2/2022 | Seykora et al. |
| 2022/0087819 A1 | 3/2022 | Robinson et al. |
| 2022/0133336 A1 | 5/2022 | Tsai et al. |
| 2022/0133497 A1 | 5/2022 | Dewey et al. |
| 2022/0133498 A1 | 5/2022 | Josse et al. |
| 2022/0133499 A1 | 5/2022 | Josse et al. |
| 2022/0218325 A1 | 7/2022 | Josse |
| 2022/0313450 A1 | 10/2022 | Donohoe et al. |
| 2022/0387184 A1 | 12/2022 | Josse et al. |
| 2022/0409397 A1 | 12/2022 | Hayes et al. |
| 2023/0015512 A1 | 1/2023 | Eisen et al. |
| 2023/0027836 A1 | 1/2023 | Predick et al. |
| 2023/0137358 A1 | 5/2023 | Hayes et al. |

FOREIGN PATENT DOCUMENTS

| | | | |
|---|---|---|---|
| EP | 0 767 636 A1 | 4/1997 | |
| EP | 0 880 950 A1 | 12/1998 | |
| EP | 0 857 042 B1 | 11/2001 | |
| EP | 1 442 732 A1 | 8/2004 | |
| EP | 1 124 512 B1 | 9/2004 | |
| EP | 1 107 711 B1 | 10/2004 | |
| EP | 1 506 753 A1 | 2/2005 | |
| EP | 1 459 711 B1 | 7/2007 | |
| EP | 2954860 A2 | 12/2015 | |
| EP | 3031424 A1 | 6/2016 | |
| EP | 3 069 694 A1 | 9/2016 | |
| EP | 3213720 A1 | 9/2017 | |
| FR | 2781998 A1 | 2/2000 | |
| FR | 3082115 A1 | 12/2019 | |
| GB | 2 377 387 A | 1/2003 | |
| KR | 102192022 B1 | 12/2020 | |
| WO | 92/14423 A1 | 9/1992 | |
| WO | 97/ 00054 A1 | 1/1997 | |
| WO | 99/ 26562 A1 | 6/1999 | |
| WO | 99/66867 A1 | 12/1999 | |
| WO | 00/12033 A1 | 3/2000 | |
| WO | 00/25706 A1 | 5/2000 | |
| WO | 00/ 49977 A1 | 8/2000 | |
| WO | WO-0074608 A1 * | 12/2000 | ........... A61F 2/4465 |
| WO | 02/19952 A1 | 3/2002 | |
| WO | 03/105673 A2 | 12/2003 | |
| WO | 2006116850 A1 | 11/2006 | |
| WO | 2012139022 A2 | 10/2012 | |
| WO | 2014/133755 A1 | 9/2014 | |
| WO | 2015063721 A1 | 5/2015 | |
| WO | 2015198335 A1 | 12/2015 | |
| WO | 2016057940 A1 | 4/2016 | |
| WO | 2016/205607 A1 | 12/2016 | |
| WO | 2017/168208 A1 | 10/2017 | |
| WO | 2018049227 A1 | 3/2018 | |
| WO | 2021055323 A1 | 3/2021 | |

OTHER PUBLICATIONS

International Search Report and Written Opinion in Application No. PCT/US2022/016831 dated Sep. 29, 2022.
International Search Report, and Written Opinion for Application. No. PCT/US2019/019067, dated Jun. 3, 2019.
International Search Report and Written Opinion for Application No. PCT/US2019/019060, dated Jun. 5, 2019.
Chinese Office Action in Application No. 201980010758.4 dated Sep. 16, 2023.
International Search Report and Written Opinion in Application No. PCT/US2022/027200 dated Aug. 19, 2022.
International Search Report and Written Opinion, PCT/IB2020/000942, Dated Aug. 10, 2021.
International Search Report and Written Opinion in Application No. PCT/US2022/016809 dated Jul. 27, 2022.
International Search Report and Written Opinion in Application No. PCT/US2022/027695 dated Jul. 27, 2022.

(56) References Cited

OTHER PUBLICATIONS

International Search Report and Written Opinion, PCT/IB2020/000932, Dated Jul. 29, 2021.
Chinese Office Action in Application No. 201980010758.4 dated Jun. 16, 2023.
International Search Report and Written Opinion in Application No. PCT/US2022/030094 dated Sep. 16, 2022.
International Search Report and Written Opinion in Application No. PCT/IB2023/057720 dated Nov. 8, 2023.
International Search Report and Written Opinion in Application No. PCT/IB2024/054985 dated Sep. 10, 2024.

\* cited by examiner

100

100

200

200

RHOMBOID SHAPED IMPLANTS

CROSS-REFERENCE TO RELATED APPLICATIONS

This application is a continuation in part of U.S. application Ser. No. 17/246,968, titled Unibody Dual Expanding Interbody Implant, filed May 3, 2021; U.S. application Ser. No. 17/307,578 titled Externally Driven Expandable Interbody and Related Methods, filed May 4, 2021; and U.S. application Ser. No. 17/331,058, titled Dual Wedge Implant, filed May 26, 2021. The entire disclosure of each is incorporated herein in its entirety.

FIELD

The present technology is generally related to implants for use in a medical procedure related to the spine. In some embodiments, disclosed implants may have a rhomboid like shape and may be used in an anterior cervical discectomy and fusion (ACDF) procedure although other uses in other areas of the spine and other orthopedic uses are also contemplated.

BACKGROUND

Implants for the spine may be positioned between adjacent vertebrae of a patient include a superior endplate and an inferior endplate roughly having a rectangular and/or square configuration. Additionally, implants for the spine may include bone screw apertures extending through the superior endplate and/or inferior endplate for securing a corresponding bone screw into an adjacent vertebra.

SUMMARY

The techniques of this disclosure generally relate to an implant for the spine having a rhomboid like shape. A rhomboid or near-rhomboid shaped interbody as disclosed herein may more closely conform to the natural human anatomy of a disc space than conventional rectangular implants, particularly in the cervical area of the spine. Additionally, in various embodiments, the implant may, for example, orient a superior bone screw at an angle that is substantially or more closely approximately perpendicular with respect to a plane of the superior endplate. Similarly, the implant may, for example, orient an inferior bone screw at an angle that is substantially or more closely approximately perpendicular with respect to a plane of the inferior endplate.

In various embodiments, a spinal implant is disclosed. The spinal implant may include a body extending from a proximal surface to a distal surface in a proximal-to-distal direction, extending from a first lateral surface to a second lateral surface in a widthwise direction, and extending from a superior surface to an inferior surface in a vertical direction, for example. In various embodiments, the proximal surface extends from a first lower end thereof to a first upper end thereof a first distance, and the distal surface extends from a second lower end thereof to a second upper end thereof a second distance, for example. Additionally, in various embodiments, the superior surface extends from the first upper end of the proximal surface to the second upper end of the distal surface a third distance, the third distance being defined between a central endpoint of the first upper end of the proximal surface to a central endpoint of the second upper end of the distal surface, for example. Furthermore, in various embodiments, the inferior surface extends from the first lower end of the proximal surface to the second lower end of the distal surface a fourth distance, the fourth distance being defined by a central endpoint of the first lower end of the proximal surface to a central endpoint of the second lower end of the distal surface, for example. In some embodiments, the first distance is greater than the second distance, and the third distance is less than the fourth distance.

In various embodiments, a rhomboid or near-rhomboid shaped spinal implant is disclosed. The implant may include a body extending from a proximal surface to a distal surface in a proximal-to-distal direction, extending from a first lateral surface to a second lateral surface in a widthwise direction, and extending from a superior surface to an inferior surface in a vertical direction, for example. In various embodiments, the proximal surface is substantially planar, or curved, and defines a proximal plane, the distal surface is substantially planar, or curved, and defines a distal plane, the superior surface is substantially planar, or curved (e.g. convex) and defines a superior plane, and the inferior surface is substantially planar, or curved (e.g. convex), and defines an inferior plane, for example. In various embodiments, a first intersection of the proximal plane and the superior plane includes a first interior angle that is greater than 90 degrees, and a second intersection of the distal plane and the superior plane includes a second interior angle that is less than 90 degrees, for example. Additionally, in various embodiments, a third intersection of the proximal plane and the inferior plane includes a third interior angle that is less than 90 degrees, and a fourth intersection of the distal plane and the inferior plane includes a fourth interior angle that is greater than 90 degrees, for example.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
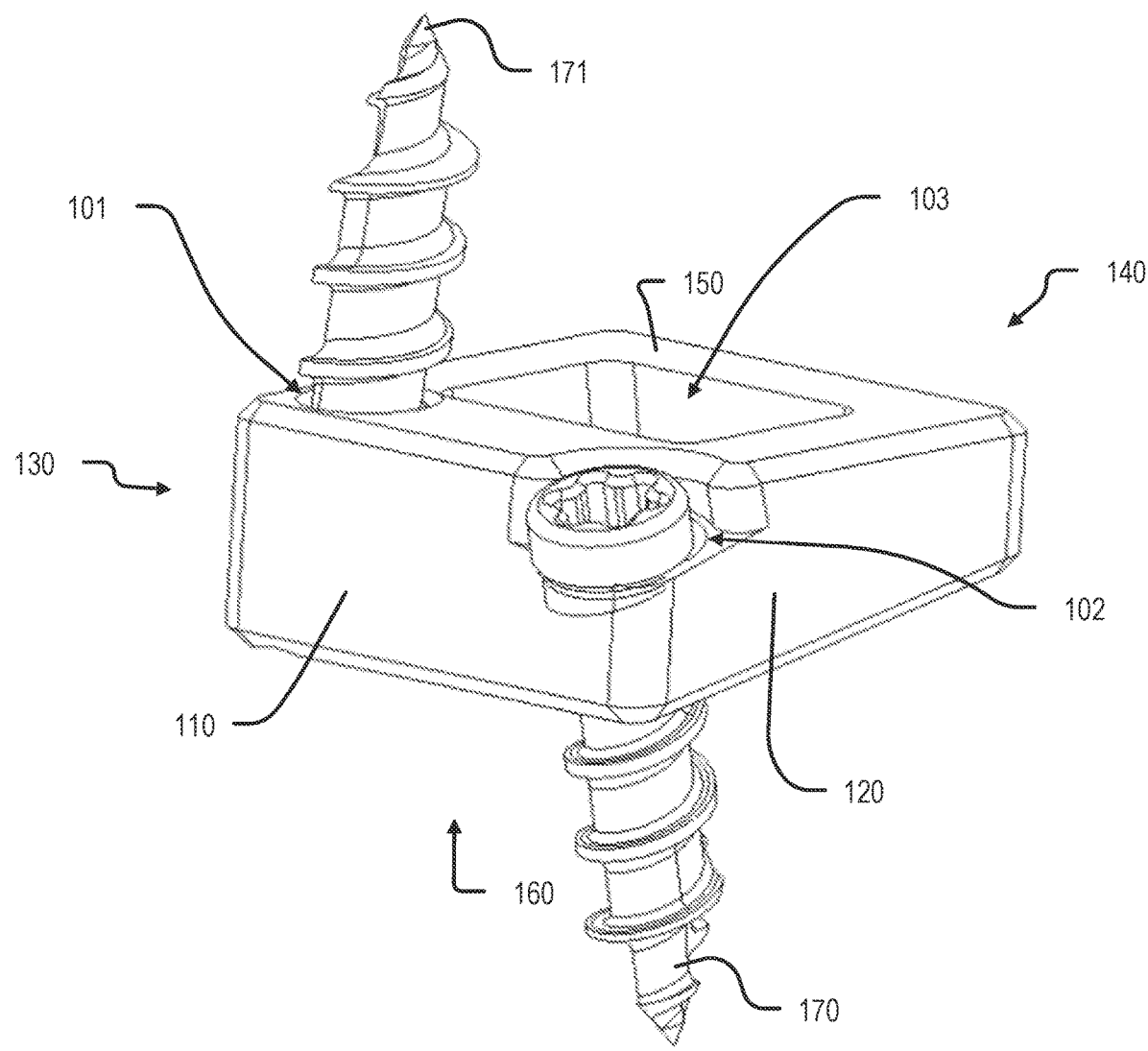
FIG. 1 is a perspective view of an implant.

Embodiments of the present disclosure relate generally, for example, to spinal interbody implants, and more particularly, to interbody implants that have a rhomboid like shape. Embodiments of the devices and methods are described below with reference to the Figures.

The following discussion omits or only briefly describes certain components, features and functionality related to medical implants, installation tools, and associated surgical techniques, which are apparent to those of ordinary skill in the art. It is noted that various embodiments are described in detail with reference to the drawings, in which like reference numerals represent like parts and assemblies throughout the several views, where possible. Reference to various embodiments does not limit the scope of the claims appended hereto because the embodiments are examples of the inventive concepts described herein. Additionally, any example(s) set forth in this specification are intended to be non-limiting and set forth some of the many possible embodiments applicable to the appended claims. Further, particular features described herein can be used in combination with other described features in each of the various possible combinations and permutations unless the context or other statements clearly indicate otherwise.

Terms such as "same," "equal," "planar," "coplanar," "parallel," "perpendicular," etc. as used herein are intended to encompass a meaning of exactly the same while also including variations that may occur, for example, due to manufacturing processes. The term "substantially" may be used herein to emphasize this meaning, particularly when the described embodiment has the same or nearly the same functionality or characteristic, unless the context or other statements clearly indicate otherwise.

Figure 2A:
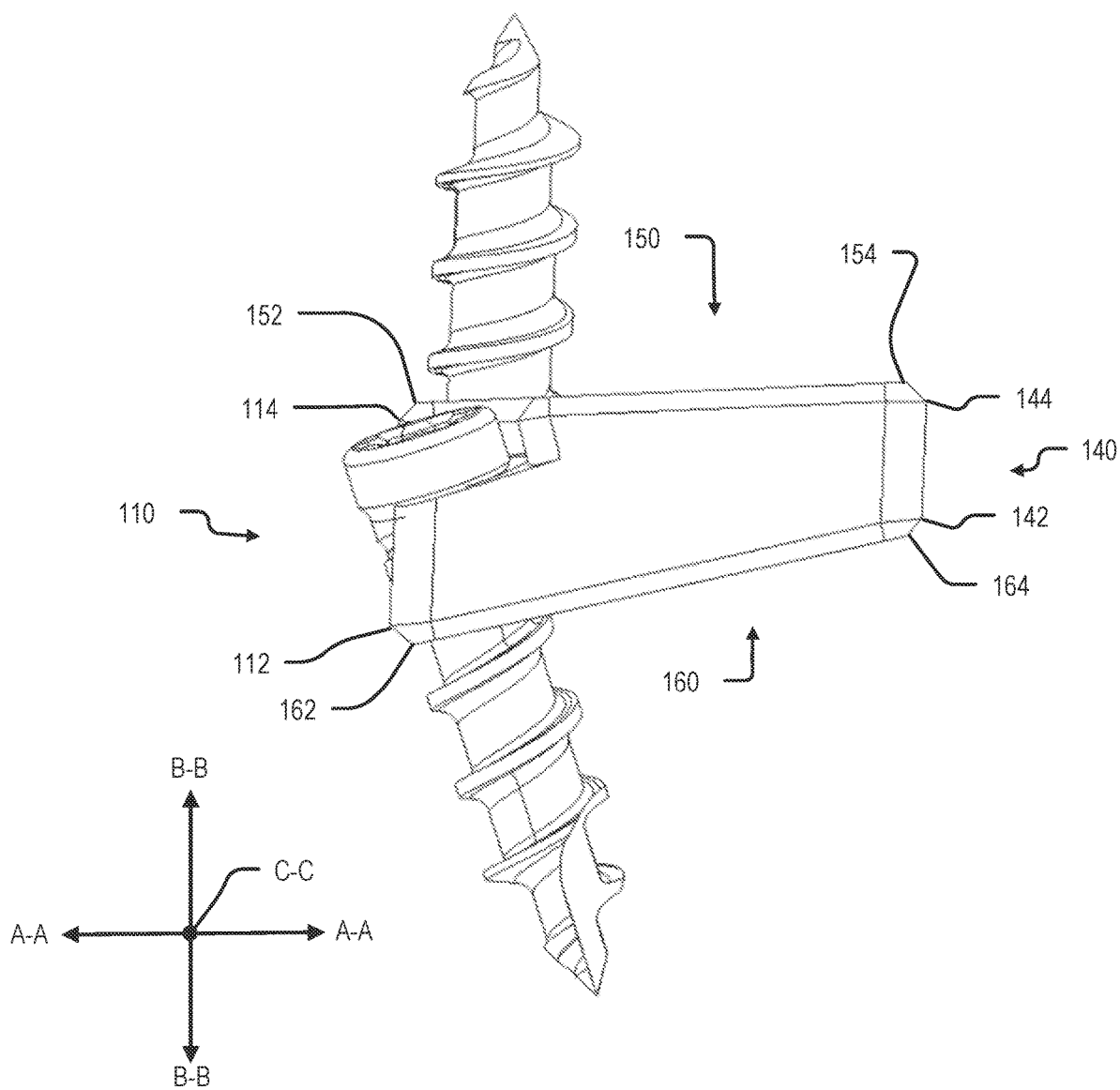
FIG. 2A is a first side view of the implant of FIG. 1.
Figure 2B:
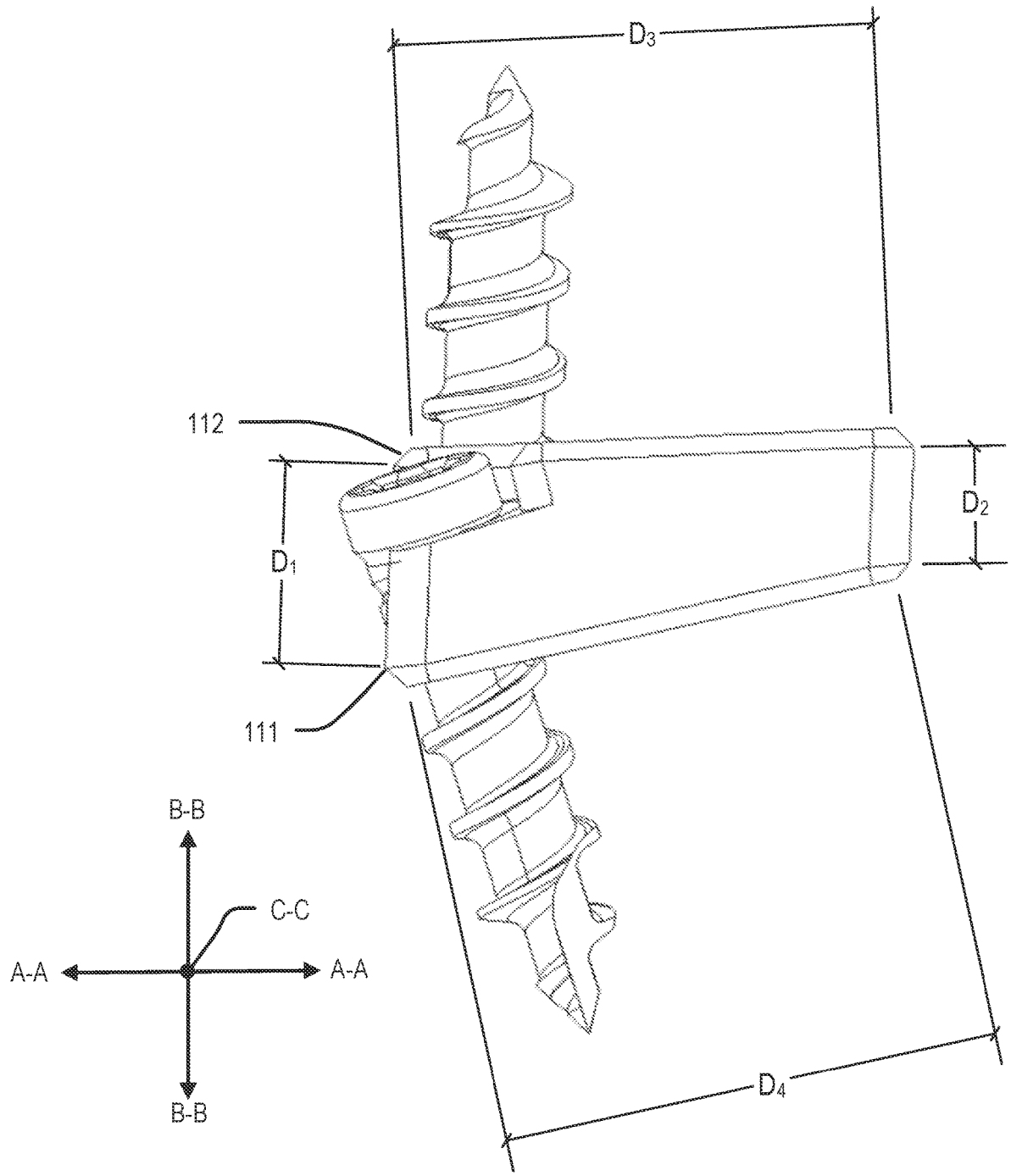
FIG. 2B is a second side view of the implant of FIG. 1.
Figure 2C:
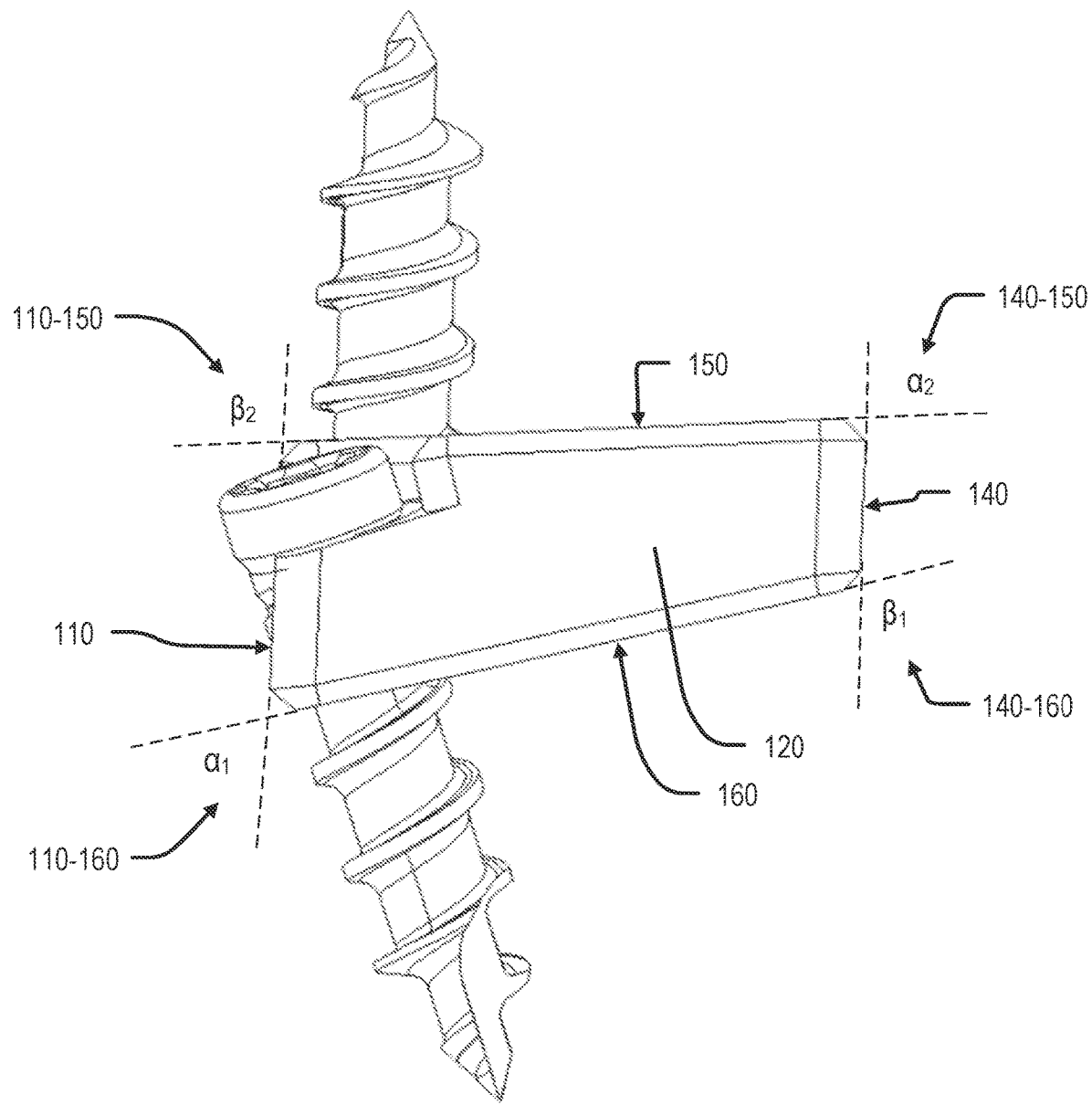
FIG. 2C is a third side view of the implant of FIG. 1.
Figure 2D:
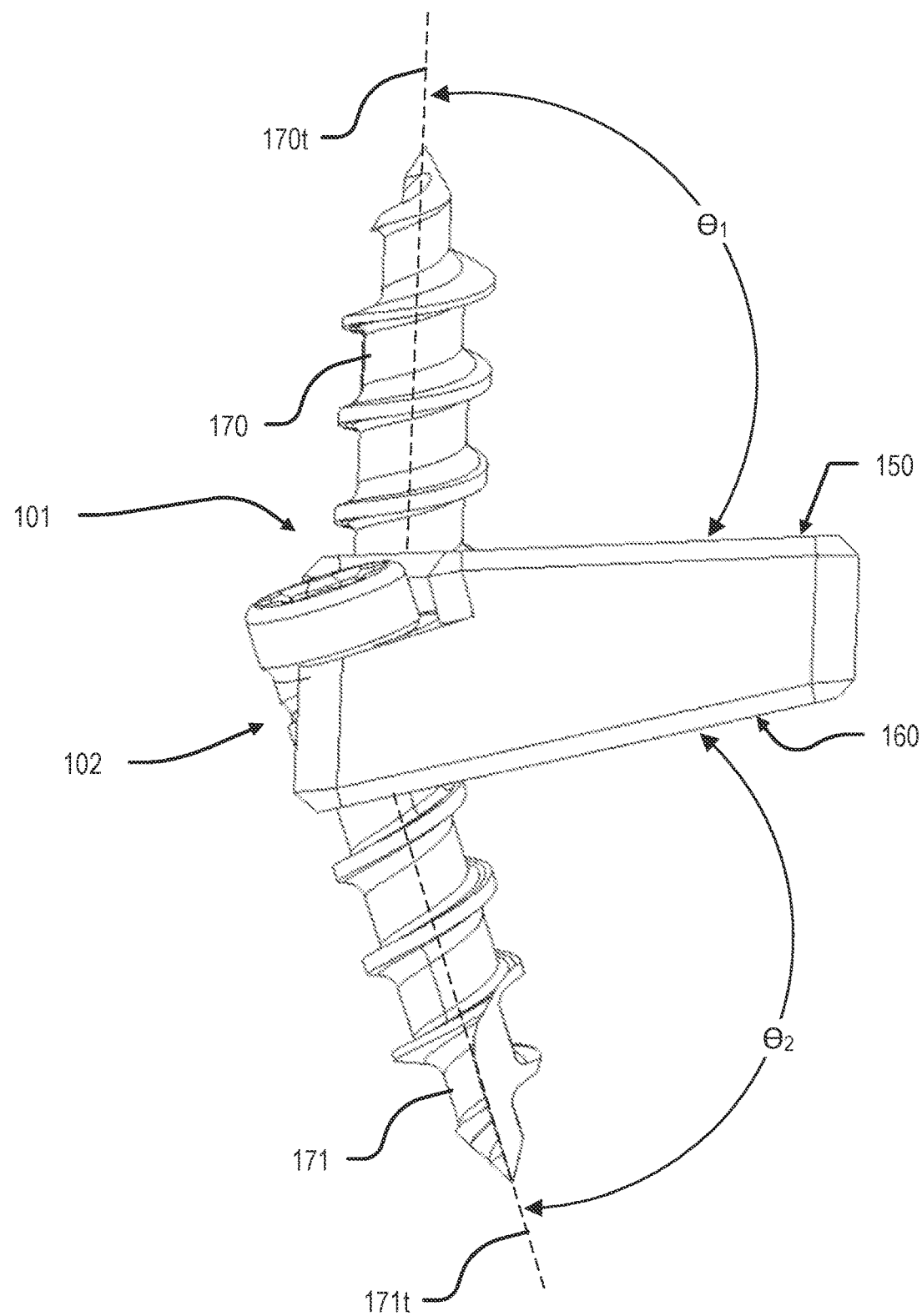
FIG. 2D is a fourth side view of the implant of FIG. 1.
Figure 3:
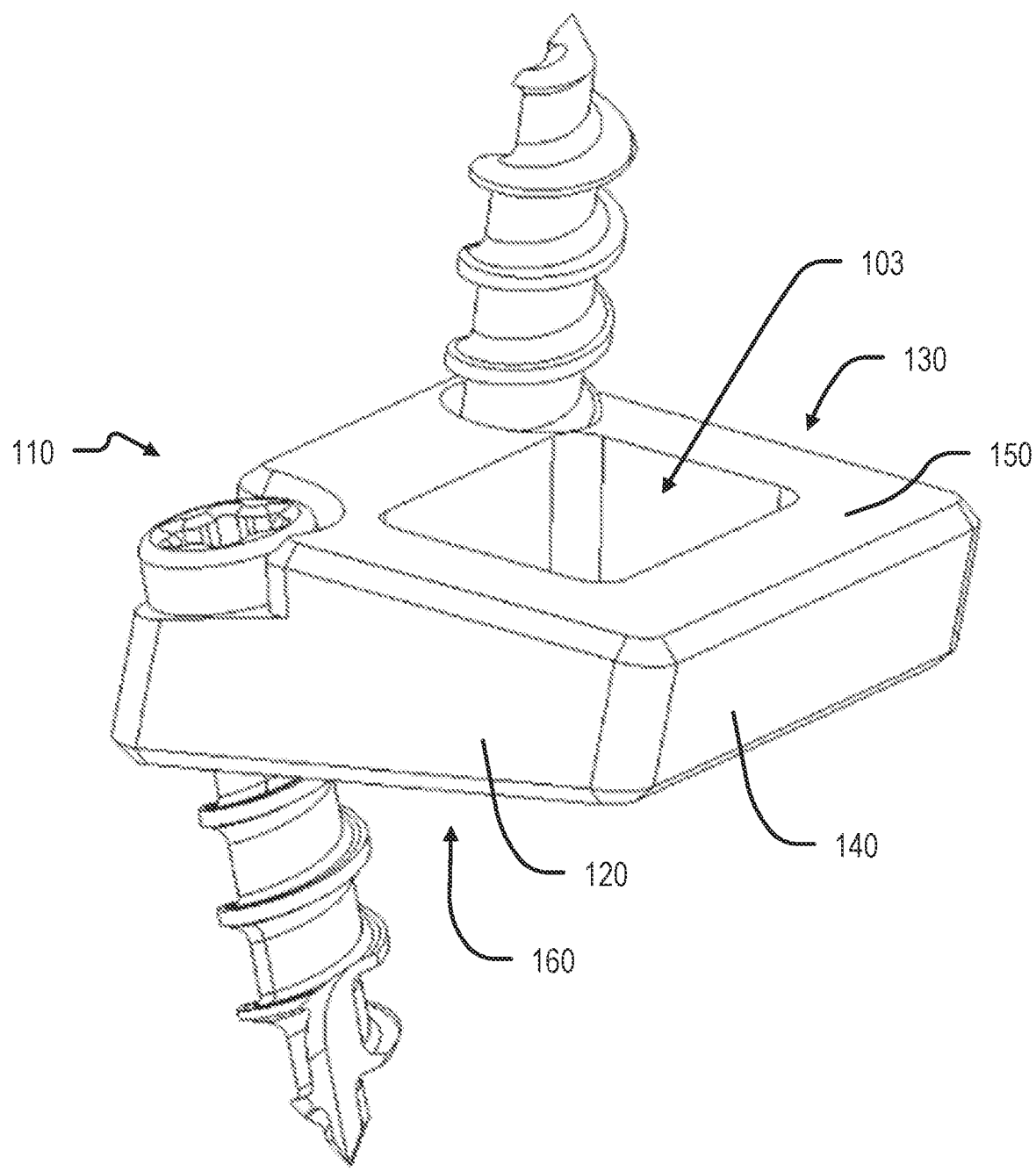
FIG. 3 is an alternate perspective view of an implant.

Referring generally to FIGS. 1-3 a first embodiment of a spinal implant 100 is disclosed. Spinal implant 100 may have a general shape approximating the shape of a rhomboid, for example. In a side view, example implants 100 may be shaped like a parallelogram in which adjacent sides are of unequal lengths and interior angles between the adjacent sides are non-right angled, i.e., have an approximately rhomboid shaped configuration. Example implants 100 may be of the expandable type or the non-expandable type. Those that do expand may form a general shape approximating the shape of a rhomboid in the expanded configuration, at least in cross section. Various surfaces of the implant 100 may be planar and/or concave, convex, undulating, etc. At least one advantage of implant 100 having a cross sectional shape that generally approximates a rhomboid is that implant 100 may better or more closely conform to and/or approximate a disc space of a patient, for example. For example, the cervical area of the spine may include disc spaces that are shaped like a trapezoid and a rhombus shaped implant may better support the disc space than a conventional square or rectangular shaped implant. Disclosed implants facilitate the maximization of endplate coverage within the disc space without protruding anteriorly, posteriorly, and/or into the spinal canal, for example.

Implant 100 may be a unibody implant formed of a monolithic structure, or body, for example. Implant 100 may include a body having six dominant surfaces or sides, for example. Implant 100 may include proximal surface 110, first lateral surface 120, second lateral surface 130, distal surface 140, superior surface 150, and inferior surface 160. In some embodiments, superior surface 150 may be a surface of a superior endplate and inferior surface 160 may be a surface of an inferior endplate. The body of implant 100 may extend from proximal surface 110 to distal surface 140 in a proximal-to-distal direction A-A, extend from first lateral surface 120 to a second lateral surface 130 in a widthwise direction C-C, and extend from a superior surface 150 to an inferior surface 160 in a vertical direction B-B, for example (see FIG. 2A). In the example embodiment of FIG. 1, it is shown that a first bone screw aperture 101 extends through the superior surface 150 and a second bone screw aperture 102 extends through the inferior surface 160.

Referring to FIG. 2A, the proximal surface 110 may extend from a first lower end 112 to a first upper end 114, and the distal surface 140 may extend from a second lower end 142 to a second upper end 144, for example. The superior surface 150 may extend from a first proximal end 152 thereof, to a first distal end 154 thereof, and the inferior surface 160 may extend from a second proximal end 162 thereof to a second distal end 164 thereof, for example. In various embodiments, the edges of implant 100 may be chamfered, angled, rounded, and/or smooth. For example, the edge of implant 100 where proximal surface 110 meets the superior surface 150 may comprise a chamfered edge including both first upper end 114 of proximal surface 110 and end 152 of superior surface 150, for example. Similarly, the edge of implant 100 where distal surface 140 meets the superior surface 150 may comprise a chamfered edge including both second upper end 144 of distal surface 140 and end 154 of superior surface 150, for example. Likewise, the edge of implant 100 where proximal surface 110 meets inferior surface 160 may comprise a chamfered edge including both first lower end 112 of proximal surface 110 and end 162 of inferior surface 160, for example. Similarly, the edge of implant 100 where distal surface 140 meets the inferior surface 160 may comprise a chamfered edge including both second lower end 142 of distal surface 140 and end 164 of inferior surface 160, for example. In other embodiments, a chamfered edge may not be provided, or may be selectively provided, and the various edges may be the same, substantially the same, and/or similar as described above. Furthermore, in some embodiments, various surfaces described above having edges adjoining the chamfered edge may be coextensive.

In some embodiments, a transition from one surface to the next adjoining surface may not include a hard edge delimiting the two surfaces. For example, a transition from a dominant face of one surface to the next adjoining dominant face of another surface may be a smooth and relatively subtle transition. The smooth and/or relatively subtle transition may be a chamfered edge, a curved edge, a bulbous edge, or the like, for example. In some embodiments, the superior surface 150 may be convex and the curvature of the superior surface 150 may match the curvature of the endplate of an adjacent vertebrae and the transition from the superior surface 150 to the first lateral surface 120 and second lateral surface 130 may be a smoother and/or gentler transition than what is shown in FIG. 2A.

In FIG. 2B, a spinal implant 100 is illustrated. FIG. 2B is the same side view of implant 100 as FIG. 2A although with different geometrical properties emphasized. For example, a first distance $D_1$ of proximal surface 110 may be understood as a distance from first lower end 112 to first upper end 114 in the vertical direction B-B. For example, a first point on first lower end 112 that is laterally aligned in the widthwise direction C-C with a second point on first upper end 114, i.e., a corresponding point. A second distance $D_2$ of distal surface 140 may be understood as a distance from second lower end 142 to second upper end 144 in the vertical direction B-B. For example, a third point on second lower end 142 that is laterally aligned in the widthwise direction C-C with a fourth point on second upper end 144.

Similarly, a third distance $D_3$ of superior surface 150 may be understood as a distance from end 152 to end 154 (and/or also from first upper end 114 to second upper end 144) in the proximal-to-distal direction A-A. For example, a fifth point on end 152 that is laterally aligned in the widthwise direction C-C with a sixth point on first upper end 114, i.e., a corresponding point. A fourth distance $D_4$ of inferior surface 160 may be understood as a distance from end 162 to end 164. For example, a seventh point on end 162 that is laterally aligned in the widthwise direction C-C with an eighth point on end 164. In various embodiments, the fourth distance $D_4$ is greater than the first distance $D_1$, second distance $D_2$, and third distance $D_3$, for example. Additionally, the third distance may be greater than the first distance $D_1$ and the second distance $D_2$. Furthermore, the first distance $D_1$ may be greater than the second distance $D_2$. This relationship of distances may result in an implant 100 having a rhomboid and/or substantially rhomboid like shape. For example, in the side view of FIG. 2B the implant 100 is shaped like a rhomboid.

In various embodiments, the proximal surface 110, first lateral surface 120, second lateral surface 130, distal surface 140, superior surface 150, and inferior surface 160 may be substantially planar. In some embodiments, the proximal surface 110, first lateral surface 120, second lateral surface 130, distal surface 140, superior surface 150, and inferior surface 160 may include a portion thereof that may be substantially planar. For example, an end portion thereof and/or a central medial portion thereof. As illustrated in FIG. 2C, an extension of the dominant contour (and/or plane) of inferior surface 160 may intersect with an extension of the dominant contour of proximal surface 110 at point 110-160 and form a first acute angle $\alpha_1$, i.e., an angle less than 90 degrees. Similarly, an extension of the dominant contour of inferior surface 160 may intersect with an extension of the dominant contour of distal surface 140 at point 140-160 and form a first obtuse angle $\beta_1$, i.e., an angle greater than 90 degrees and less than 180 degrees. Additionally, an extension of the dominant contour of superior surface 150 may intersect with an extension of the dominant contour of proximal surface 110 at point 110-150 and form a second obtuse angle $\beta_2$. Furthermore, an extension of the dominant contour of superior surface 150 may intersect with an extension of the dominant contour of distal surface 140 at point 140-150 and form a second acute angle $\alpha_2$. In various embodiments, the above angles may be established at any point where the respective planes as explained above interest. Although an outside angle is labeled, those with skill in the art will appreciate that the labeled outside angle directly corresponds to the interior angle as well. Additionally, in some embodiments, the above angles are established at a point or points corresponding in space to the lateral ends adjacent the first lateral surface 120, and/or alternatively adjacent the second lateral surface 130, for example. Furthermore, the above angles may be established at a junction of the corresponding surfaces and correspond to an internal angle between the respective surfaces in the same, similar, and/or substantially the same way.

Consistent with the above disclosure, those with skill in the art will understand that the overall shape of implant 100 may be a generally rhomboid like shape when viewed from the side, and/or in a side view of a cross section through implant 100 in the proximal-to-distal direction and that the particular angles shown in the example embodiments may be different. For example, an exact angle between the edge portion of the superior surface 150 and the edge portion of the proximal surface 110 is not necessarily "obtuse" but rather the dominant contour of the superior surface 150 and the dominant contour of the proximal surface 110 intersect in 3D space to form an obtuse angle. Similarly, an exact angle between the edge portion of the inferior surface 160 and the proximal surface 110 is not necessarily "acute" but rather the dominant contour of the inferior surface 160 and the dominant contour of the proximal surface 110 intersect in 3D space to form an acute angle. In some embodiments, a dominant contour of a particular surface may be calculated as an average of various discrete contours of the same surface. For example, a dominant contour of the superior surface 150 may be calculated by taking an average of ten contour lines extending in a parallel direction from the proximal side of the superior surface 150 to the distal side of the superior surface 150, for example. Furthermore, a similar edge-to-edge averaging of contours of a different surface may be performed in like manner on any of the various surfaces discussed herein with more or less contour lines, e.g., any number of contour lines from about 2 to about 100 depending solely on the precision required for the target position of implant 100 between two particular vertebrae of a patient.

In the example embodiment of FIG. 2D, it is shown that a first bone screw aperture 101 extends through the superior surface 150 in a superior direction that is substantially parallel to the vertical direction, for example. Similarly, it is shown that a second bone screw aperture 102 extends through the inferior surface 160 in an inferior direction that is substantially parallel to the vertical direction. First bone screw aperture 101 may be formed at a corner of implant 100 formed partly in the proximal surface 110 and first lateral surface 120, for example. First bone screw aperture 101 may comprise a circular through hole, a tapering through hole, or a conical through hole that orients a first bone screw 170 in a pre-stablished trajectory 170$t$, for example. In various embodiments, trajectory 170$t$ may project away from the superior surface 150 at an angle $\Theta_1$ that is approximately and/or substantially perpendicular to superior surface 150, e.g., about 80-90 degrees. It is contemplated that trajectory 170$t$ may be angled slightly in the distal direction and/or towards a medial portion of implant 100 as well. Similarly, second bone screw aperture 102 may comprise a circular through hole, a tapering through hole, or a conical through hole that orients a second bone screw 171 in a pre-stablished trajectory 171$t$, for example. In various embodiments, trajectory 171$t$ may project away from the inferior surface 160 at an angle $\Theta_2$ that is approximately and/or substantially perpendicular to inferior surface 160, e.g., about 80-90 degrees. It is contemplated that trajectory 171$t$ may be angled slightly in the distal direction and/or towards a medial portion of implant 100 as well. In this way, trajectories 170$t$, 171$t$ may converge towards a central portion of implant 100 from the proximal side of implant 100 towards the distal side of implant 100, for example. At least one advantage of bone screw apertures 101, 102 defining trajectories 170$t$, 171$t$ as explained above is that the substantially perpendicular orientation increases the relative amount of shear loading the bone screws 170, 171 can absorb across the disc space compared to an axial force applied to the bone screws 170, 171, for example. Additionally, in various embodiments, the substantially or approximately perpendicular orientation facilitates the bone screws 170, 171 being secured to patient anatomy predominantly, mostly, and/or entirely within the anterior rim and/or cortical bone, which is generally considered a relatively strong section of bone.

FIG. 3 is an additional perspective view of implant 100 showing the features and characteristics explained above. Additionally, FIG. 3 illustrates a bone graft aperture 103 that may be formed in the center of implant 100, for example in a medial position. Bone graft aperture 103 may extend through the superior surface 150 and inferior surface 160 and be shaped like a square, rectangle, oval, circle, or the like.

Figure 4:
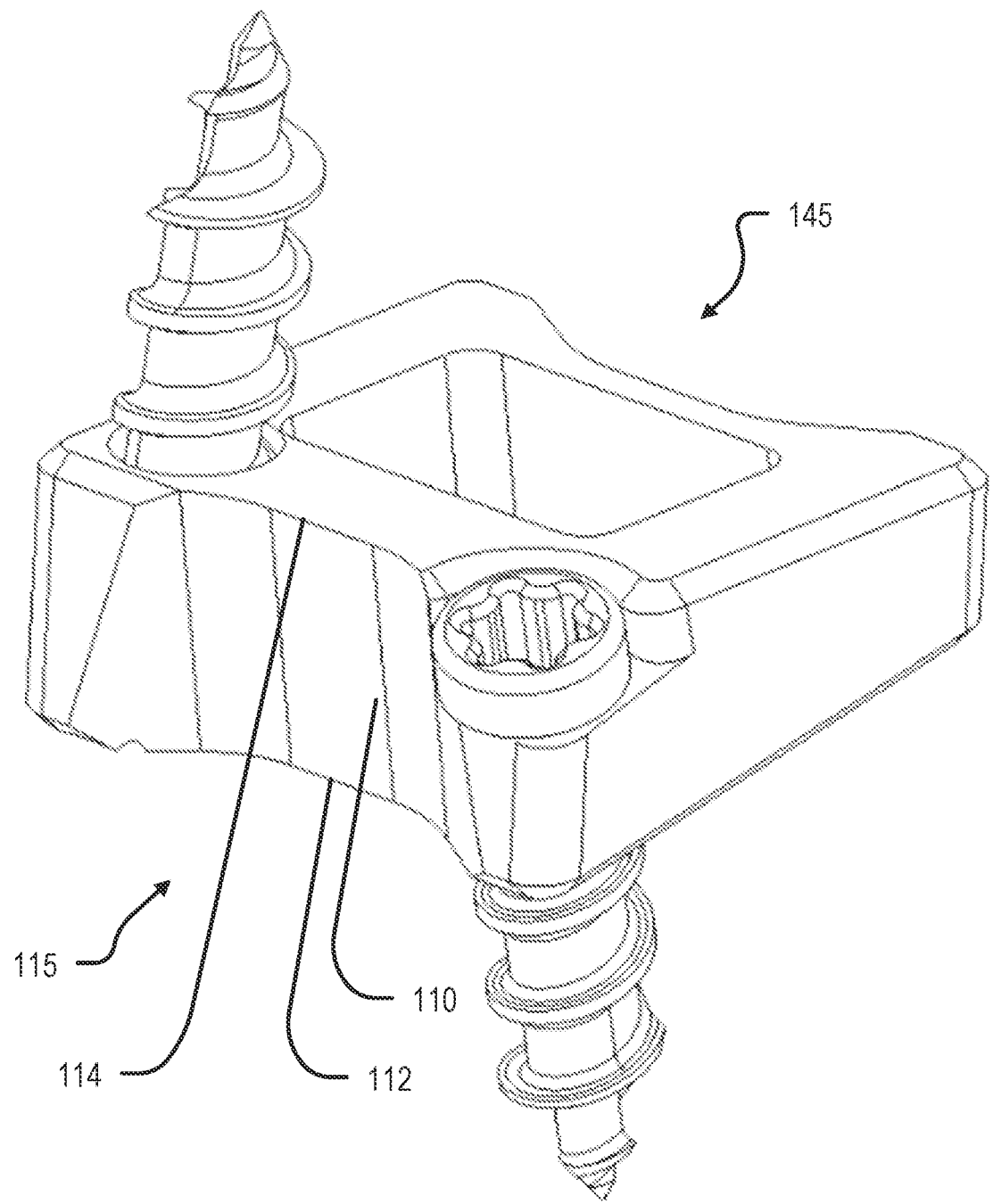
FIG. 4 is a perspective view of an alternate implant.
Figure 5:
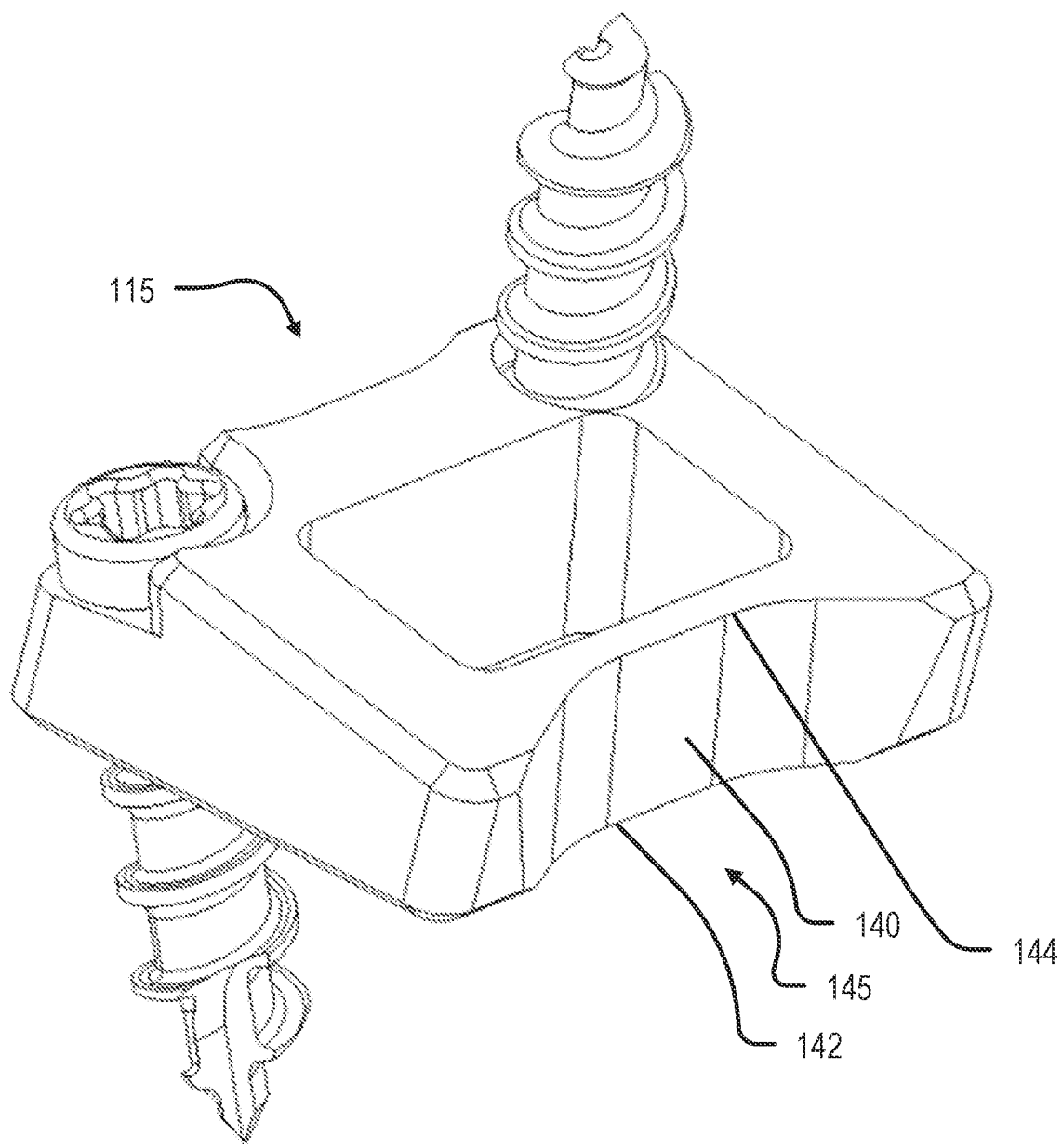
FIG. 5 is an alternate perspective view of the implant of FIG. 4.

FIGS. 4-5 are perspective views of an alternate implant 200. Alternate implant 200 may have the same, similar, and/or substantially the same characteristics as explained above with respect to implant 100. Additionally, proximal surface 110 may include a relatively wide curved surface 115 (also referred to as a scallop 115), for example. In various embodiments, the proximal surface 110 may be substantially defined by a first curved surface 115 that arcs inward with respect to the distal surface 140 and extends in a vertical direction from the first lower end 112 to the first upper end 114, for example. Similarly, in various embodiments, distal surface 140 may include a relatively wide curved surface 145 (also referred to as a scallop 145), for example. In various embodiments, the distal surface 140 may be substantially defined by a second curved surface 145 that arcs inward with respect to the proximal surface 110 and extends in a vertical direction B-B from the first lower end 112 to the first upper end 114, for example. At least one advantage of curved surfaces 115, 145 is that they may be curved to avoid delicate anatomy such as the spinal cord and/or other sensitive patient tissue.

An additional advantage of curved surfaces 115, 145 is that they may accommodate and/or conform to additional medical hardware, such as an anterior plate for bone screws or the like (not illustrated). For example, curved surface 115 may allow access to install and/or tighten the bone screws to the adjacent vertebrae with a retaining plate in place. For example still, the curved surface 115 may allow the anterior plate to be positioned above the anterior face of the patient vertebrae a first distance and allow eyelets to be positioned proud by a second distance. In some embodiments, the first and second distances may be substantially the same which may allow the bone screws to be oriented perpendicular and/or substantially perpendicular to the patient VB which may allow the bone screws to be secured to cortical bone because the anterior plate has positioned the bone screws far enough in an anterior direction, for example.

Figure 6A:
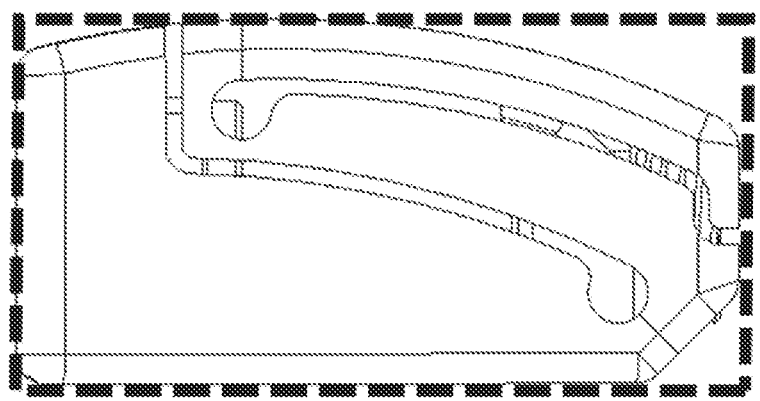
FIG. 6A is a side view of a unibody implant in a contracted configuration.
Figure 6B:
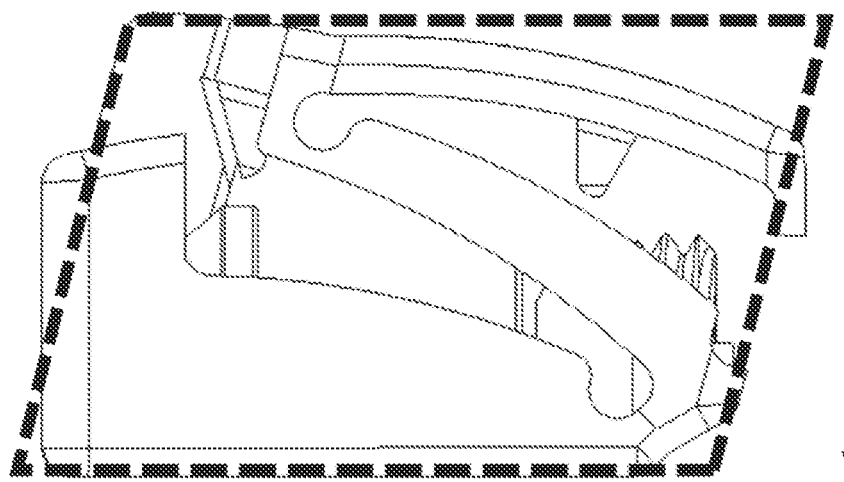
FIG. 6B is a side view of the implant of FIG. 6A in an expanded configuration.

FIG. 6A is a side view of a unibody implant 300 in a contracted configuration and FIG. 6B is a side view of the unibody implant 300 in an expanded configuration. Unibody implant 300 may include the same, substantially the same, and/or similar features and characteristics as described in detail in U.S. application Ser. No. 17/246,968, titled Unibody Dual Expanding Interbody Implant, the entire contents of which are incorporated herein. Additionally, as illustrated, unibody implant 300 approximates a rhomboid like shape (in cross section). In some embodiments, unibody implant 300 may approximate a rhomboid like shape in an expanded position, a collapsed position, and/or an intermediate position. Accordingly, various unibody implants 300 may have the same advantages as disclosed herein with respect to implants 100, and 200. Similarly, the various implants disclosed in U.S. application Ser. No. 17/307,578, titled Externally Driven Expandable Interbody and Related Methods; and U.S. application Ser. No. 17/331,058, titled Dual Wedge Implant may also have a rhomboid like shape.

It should be understood that various aspects disclosed herein may be combined in different combinations than the combinations specifically presented in the description and accompanying drawings. For example, features, functionality, and components from one embodiment may be combined with another embodiment and vice versa unless the context clearly indicates otherwise. Similarly, features, functionality, and components may be omitted unless the context clearly indicates otherwise. It should also be understood that, depending on the example, certain acts or events of any of the processes or methods described herein may be performed in a different sequence, may be added, merged, or left out altogether (e.g., all described acts or events may not be necessary to carry out the techniques).

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

What is claimed is:

1. A spinal implant, comprising:
a body extending from a proximal surface to a distal surface in a proximal-to-distal direction, extending from a first lateral surface to a second lateral surface in a widthwise direction, and extending from a superior surface to an inferior surface in a vertical direction,
wherein:
the proximal surface extends from a first lower end thereof to a first upper end thereof a first distance,
the distal surface extends from a second lower end thereof to a second upper end thereof a second distance,
the superior surface extends from the first upper end of the proximal surface to the second upper end of the distal surface a third distance, the third distance being defined between a central endpoint of the first upper end of the proximal surface to a central endpoint of the second upper end of the distal surface,
the inferior surface extends from the first lower end of the proximal surface to the second lower end of the distal surface a fourth distance, the fourth distance being defined by a central endpoint of the first lower end of the proximal surface to a central endpoint of the second lower end of the distal surface,
the first distance is greater than the second distance,
the third distance is less than the fourth distance,
in a side view, a first interior angle formed by an intersection of a dominant extension of a side edge of the proximal surface and a dominant extension of a side edge of the inferior surface defines a first acute angle,
in the side view, a second interior angle formed by an intersection of the dominant extension of the side edge of the proximal surface and a dominant extension of a side edge of the superior surface defines a first obtuse angle,
in the side view, a third interior angle formed by an intersection of a dominant extension of a side edge of the distal surface and the dominant extension of the side edge of the superior surface defines a second acute angle, and
in the side view, a fourth interior angle formed by an intersection of the dominant extension of the side edge of the distal surface and a dominant extension of the side edge of the inferior surface defines a second obtuse angle.

2. The implant of claim 1, wherein the fourth distance is greater than the first distance, the second distance, and the third distance.

3. The implant of claim 2, wherein the third distance is greater than the second distance and first distance.

4. The implant of claim 1, wherein, in a side view, the body is in a substantially rhomboid configuration.

5. The implant of claim 1, wherein the body is a unitary body.

6. The implant of claim 1, wherein the body is an expandable body and in an expanded configuration the body is in a substantially rhomboid configuration.

7. The implant of claim 1, wherein a centrally disposed graft aperture extends through the superior surface and the inferior surface in the vertical direction.

8. The implant of claim 1, further comprising at least one of: a first bone screw aperture defining a first trajectory for a first bone screw and/or a second bone screw aperture defining a second trajectory for a second bone screw.

9. The implant of claim 8, wherein the superior surface is substantially planar and the first trajectory extends away from the superior surface in a superior direction that is substantially perpendicular to the superior surface.

10. The implant of claim 8, wherein the inferior surface is substantially planar and the second trajectory extends away from the inferior surface in an inferior direction that is substantially perpendicular to the inferior surface.

11. The implant of claim 8, wherein:
the superior surface is substantially planar and the first trajectory extends away from the superior surface in a superior direction that is substantially perpendicular to the superior surface, and
the inferior surface is substantially planar and the second trajectory extends away from the inferior surface in an inferior direction that is substantially perpendicular to the inferior surface.

12. The implant of claim 1, wherein:
the proximal surface is substantially planar and defines a proximal plane,
the distal surface is substantially planar and defines a distal plane,
the superior surface is substantially planar and defines a superior plane, and
the inferior surface is substantially planar and defines an inferior plane.

13. The implant of claim 1, wherein:
the proximal surface is substantially defined by a first curved surface that arcs inward with respect to the distal surface and extends in the vertical direction from the first lower end of the proximal surface to the first upper end of the proximal surface, and
the distal surface is substantially defined by a second curved surface that arcs inward with respect to the proximal surface and extends in the vertical direction from the second lower end of the distal surface to the second upper end of the distal surface.

14. An approximately rhomboid shaped spinal implant, comprising:
a body extending from a proximal surface to a distal surface in a proximal-to-distal direction, extending from a first lateral surface to a second lateral surface in a widthwise direction, and extending from a superior surface to an inferior surface in a vertical direction,
wherein:
the proximal surface is substantially planar and defines a proximal plane,
the distal surface is substantially planar and defines a distal plane,
the superior surface is substantially planar and defines a superior plane,
the inferior surface is substantially planar and defines an inferior plane,
a first intersection of the proximal plane and the superior plane comprises a first interior angle that is greater than 90 degrees,
a second intersection of the distal plane and the superior plane comprises a second interior angle that is less than 90 degrees,
a third intersection of the proximal plane and the inferior plane comprises a third interior angle that is less than 90 degrees, and
a fourth intersection of the distal plane and the inferior plane comprises a fourth interior angle that is greater than 90 degrees.

15. The implant of claim 14, further comprising at least one of: a first bone screw aperture defining a first trajectory for a first bone screw and/or a second bone screw aperture defining a second trajectory for a second bone screw.

16. The implant of claim 15, wherein first trajectory extends away from the superior plane in a superior direction that is substantially perpendicular to the superior plane and the second target trajectory extends away from the inferior plane in an inferior direction that is substantially perpendicular to the inferior plane.

* * * * *